United States Patent
Murphy et al.

(10) Patent No.: US 7,232,809 B2
(45) Date of Patent: *Jun. 19, 2007

(54) MITOCHONDRIALLY TARGETED ANTIOXIDANTS

(75) Inventors: Michael P. Murphy, Dunedin (NZ); Robin A. J. Smith, Dunedin (NZ)

(73) Assignee: Antipodean Pharmaceuticals, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/172,916

(22) Filed: Jul. 5, 2005

(65) Prior Publication Data

US 2005/0245487 A1     Nov. 3, 2005

Related U.S. Application Data

(63) Continuation of application No. 10/722,542, filed on Nov. 28, 2003, now abandoned, which is a continuation of application No. 10/272,914, filed on Oct. 18, 2002, now abandoned, which is a continuation of application No. 09/968,838, filed on Oct. 3, 2001, now abandoned, which is a continuation of application No. 09/577,877, filed on May 25, 2000, now Pat. No. 6,331,532.

(30) Foreign Application Priority Data

Nov. 25, 1997  (NZ) .................................. 329255
Nov. 25, 1998  (WO) ................... PCT/NZ98/00173

(51) Int. Cl.
    *A61K 31/665*   (2006.01)
(52) U.S. Cl. ....................... 514/100; 514/130
(58) Field of Classification Search ................ 549/218, 549/409; 514/100, 130; 568/9, 16, 17, 644, 568/645

See application file for complete search history.

(56) References Cited

U.S. PATENT DOCUMENTS

| 3,532,667 | A  | 10/1970 | Singh |
| 6,133,322 | A  | 10/2000 | Rustin et al. |
| 6,331,532 | B1 | 12/2001 | Murphy et al. ............. 514/100 |

OTHER PUBLICATIONS

Masaki et al, "Mitochondrial Damage as a Mechanism of Cell Injury . . . ," Archives of Biochemistry and Biophysics, vol. 270, No. 2, pp. 672-680 (1989).
McKittrick et al, "Synthesis of the Yeast Anitoxidant . . . " J. Chem. Soc. Perkin Trans I, pp. 709-712 (1984).
Burns et al, "Labeling of Mitochondrial Proteins in Living Cells by the Thiol Probe," Archives of Biochemistry and Biophysics, vol. 339, No. 1, pp. 33-39 (1997).
Everett et al, "Scavenging of Nitrogen Dioxide, Thiyl, and Sulfonyl Free . . . ," J. Bio. Chem., vol. 271, No. 8, pp. 3988-3994 (1996).
Burns et al, "Synthesis and Characterization of Thiobutyltriphenylphosphonium . . . ," Archives of Biochemistry and Biophysics, vol. 322, No. 1, pp. 60-68 (1995).

*Primary Examiner*—Amelia A. Owens
(74) *Attorney, Agent, or Firm*—Seed Intellectual Property Law Group PLLC

(57) ABSTRACT

The invention provides mitochondrially targeted antioxidant compounds. A compound of the invention comprises a lipophilic cation covalently coupled to an antioxidant moiety. In preferred embodiments, the lipophilic cation is the triphenyl phosphonium cation, and the compound is of the formula $P(Ph_3)^+XR.Z^-$ where X is a linking group, Z is an anion and R is an antioxidant moiety. Also provided are pharmaceutical compositions containing the mitochondrially targeted antioxidant compounds, and methods of therapy or prophylaxis of patients who would benefit from reduced oxidative stress, which comprise the step of administering the compounds of the invention.

10 Claims, 17 Drawing Sheets

MITOCHONDRIALLY TARGETED ANTIOXIDANTS

CROSS-REFERENCES TO RELATED APPLICATIONS

This application is a continuation of U.S. patent application Ser. No. 10/722,542, filed Nov. 28, 2003, now abandoned, which is a continuation of U.S. patent application Ser. No. 10/272,914, filed Oct. 18, 2002, now abandoned. which is a continuation of U.S. patent application Ser. No. 09/968,838, filed Oct. 3, 2001, now abandoned, which is a continuation of U.S. patent application Ser. No. 09/577,877, filed May 25 2000, which issued as U.S. Pat. No. 6,331,532 on Dec. 18, 2001, which applications are incorporated herein by reference in their entireties.

TECHNICAL FIELD

The invention relates to antioxidants having a lipophilic cationic group and to uses of these antioxidants, for example, as pharmaceuticals.

BACKGROUND OF THE INVENTION

Oxidative stress contributes to a number of human degenerative diseases associated with ageing, such as Parkinson's disease, and Alzheimer's disease, as well as to Huntington's Chorea, diabetes and Friedreich's Ataxia, and to non-specific damage that accumulates with aging. It also contributes to inflammation and ischaemic-reperfusion tissue injury in stroke and heart attack, and also during organ transplantation and surgery. To prevent the damage caused by oxidative stress a number of antioxidant therapies have been developed. However, most of these are not targeted within cells and are therefore less than optimally effective.

Mitochondria are intracellular organelles responsible for energy metabolism. Consequently, mitochondrial defects are damaging, particularly to neural and muscle tissues which have high energy demands. They are also the major source of the free radicals and reactive oxygen species that cause oxidative stress inside most cells. Therefore, the applicants believe delivering antioxidants selectively to mitochondria will be more effective than using non-targeted antioxidants. Accordingly, it is towards the provision of antioxidants which may be targeted to mitochondria that the present invention is directed.

Lipophilic cations may be accumulated in the mitochondrial matrix because of their positive charge (Rottenberg, (1979) *Methods Enzymol*, 55, 547–560; Chen, (1988) *Annu Rev Cell Biol* 4, 155–181). Such ions are accumulated provided they are sufficiently lipophilic to screen the positive charge or delocalise it over a large surface area, also provided that there is no active efflux pathway and the cation is not metabolised or immediately toxic to a cell.

The focus of the invention is therefore on an approach by which it is possible to use the ability of mitochondria to concentrate specific lipophilic cations to take up linked antioxidants so as to target the antioxidant to the major source of free radicals and reactive oxygen species causing the oxidative stress.

SUMMARY OF THE INVENTION

In its broadest aspect, the invention provides a mitochondrially-targeted antioxidant which comprises a lipophilic cation covalently coupled to an antioxidant moiety, wherein the antioxidant moiety is capable of being transported through the mitochondrial membrane and accumulated within the mitochondria of intact cells, with the proviso that the compound is not thiobutyltriphenylphosphonium bromide.

Preferably, the lipophilic cation is the triphenylphosphonium cation.

Preferably, the mitochondrially-targeted antioxidant has the formula

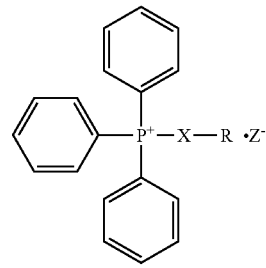

I wherein Z is an anion, X is a lining group and R is an antioxidant moiety.

Preferably, X is a $C_1$–$C_{30}$, more preferably $C_1$–$C_{20}$, carbon chain, optionally including one or more double or triple bonds, and optionally including one or more substituents (such as hydroxyl, carboxylic acid or amide groups) and/or unsubstituted or substituted alkyl, alkenyl or alkynyl side chains.

Preferably, X is $(CH_2)_n$ where n is an integer of from 1 to 20, more preferably of from about 1 to 15.

More preferably, X is an ethylene, propylene, butylene, pentylene or decylene group.

Preferably, Z is a pharmaceutically acceptable anion.

In one particularly preferred embodiment, the mitochondrially-targeted anti-oxidant of the invention has the formula

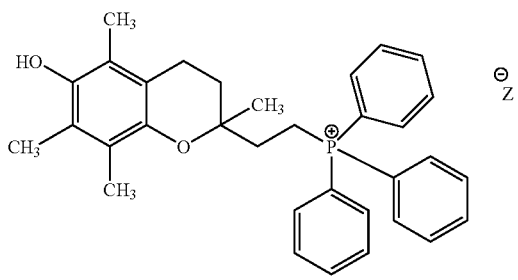

including all stereoisomers thereof.

Preferably, Z is Br. The above compound is referred to herein as "compound 1".

In another preferred embodiment, the mitochondrially-targeted antioxidant has the general formula:

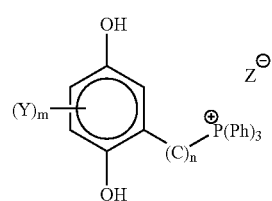

II wherein:

Z is a pharmaceutically acceptable anion, preferably a halogen, m is an integer from 0 to 3, each Y is independently selected from groups, chains and aliphatic and aromatic rings having electron donating and accepting properties, $(C)_n$ represents a carbon chain optionally including one or more double or triple bonds, and optionally including one or more substituents and/or unsubstituted or substituted alkyl, alkenyl or allyl side chains, and n is an integer of from 1 to 20.

Preferably, each Y is independently selected from the group consisting of alkoxy, thioalkyl, alkyl, haloalkyl, halo, amino, nitro, optionally substituted aryl, or, when m is 2 or 3, two Y groups, together with the carbon atoms to which they are attached, form an aliphatic or aromatic carbocyclic or heterocyclic ring fused to the aryl ring. More preferably, each Y is independently selected from method and methyl.

Preferably, $(C)_n$ is an alkyl chain of the formula $(CH_2)_n$.

In a particularly preferred embodiment, the mitochondrially-targeted antioxidant of the invention has the formula

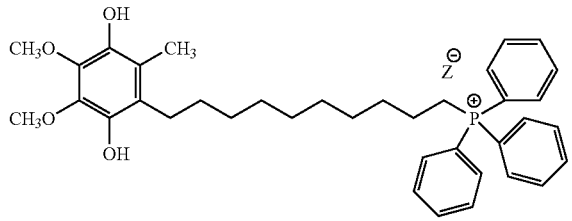

Preferably, Z is Br. The above compound is referred to herein as "mitoquinol". The oxidised form of the compound is referred to as "mitoquinone".

In a further aspect, the present invention provides a pharmaceutical composition suitable for treatment of a patient who would benefit from reduced oxidative stress which comprises an effective amount of a mitochondrially-targeted antioxidant of the present invention in combination with one or more pharmaceutically acceptable carriers or diluents.

In a further aspect, the invention provides a method of reducing oxidative stress in a cell which comprises the step of administering to said cell a mitochondrially targeted antioxidant as defined above.

In still a further aspect, the invention provides a method of therapy or prophylaxis of a patient who would benefit from reduced oxidative stress which comprises the step of administering to said patient a mitochondrially-targeted antioxidant as defined above.

Although broadly as defined above, the invention is not limited thereto but also consists of embodiments of which the following description provides examples.

DESCRIPTION OF DRAWINGS

In particular, a better understanding of the invention will be gained with reference to the accompanying drawings, in which.

DESCRIPTION OF THE INVENTION

Figure 1:
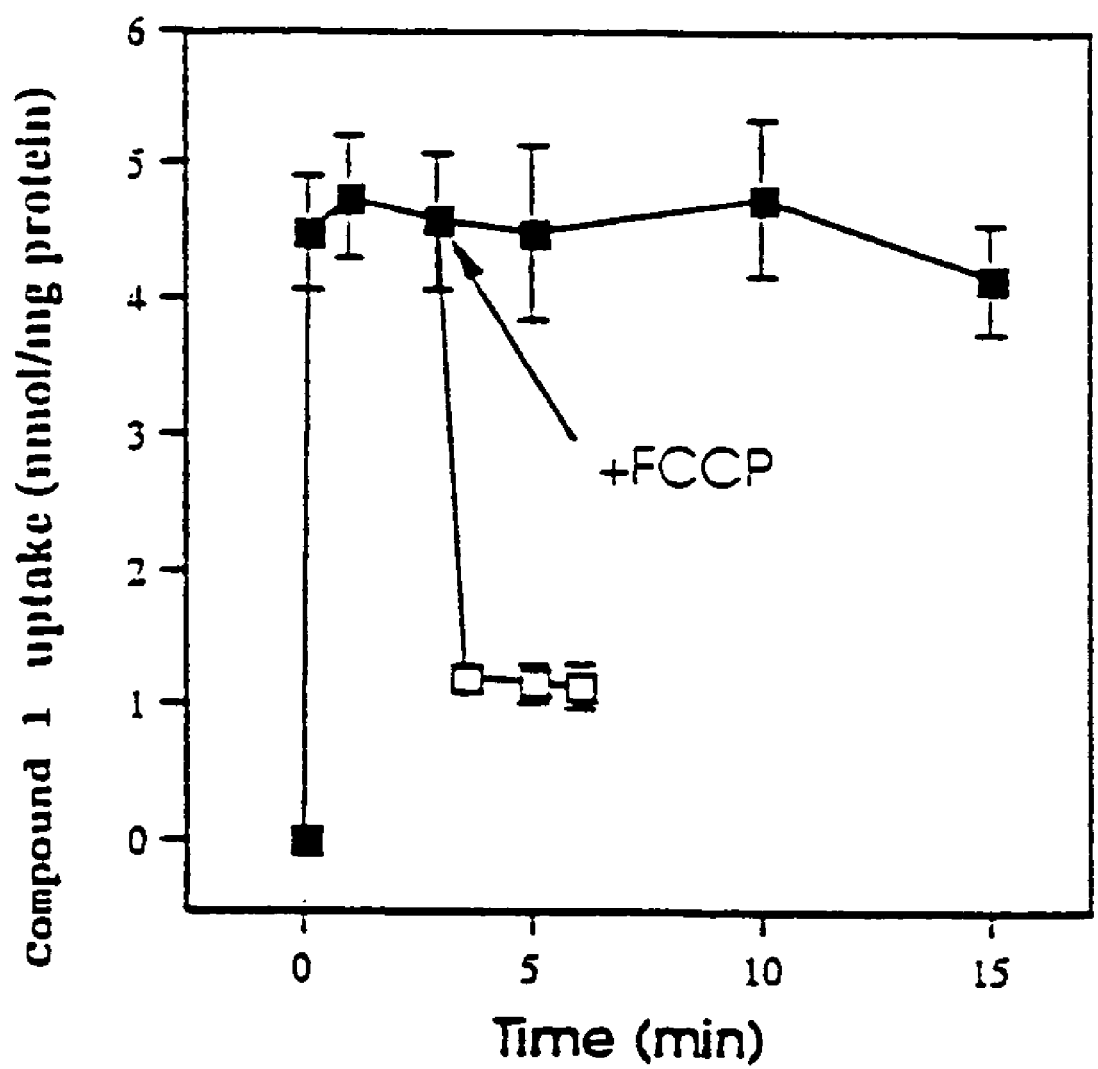
FIG. 1 is a graph which shows the uptake by isolated mitochondria of compound 1, a mitochondrially-targeted antioxidant according to the present invention.

As stated above, the focus of this invention is on the mitochondrial targeting of compounds, primarily for the purpose of therapy and/or prophylaxis to reduce oxidative stress.

Mitochondria have a substantial membrane potential of up to 180 mV across their inner membrane (negative inside). Because of this potential, membrane permeant, lipophilic cations accumulate several-hundred fold within the mitochondrial matrix.

The applicants have now found that by covalently coupling lipophilic cations (preferably the lipophilic triphenylphosphonium cation) to an antioxidant the compound can be delivered to the mitochondrial matrix within intact cells. The antioxidant is then targeted to a primary production site of free radicals and reactive oxygen species within the cell, rather than being randomly dispersed.

In principle, any lipophilic cation and any antioxidant capable of being transported through the mitochondrial membrane and accumulated within the mitochondria of intact cells, can be employed in forming the compounds of the invention. It is however preferred that the lipophilic cation be the triphenylphosphonium cation herein exemplified, and that the lipophilic cation is linked to the antioxidant moiety by a carbon chain having 1 to 30 carbon atoms, preferably 1 to 20 carbon atoms.

While it is generally preferred that the carbon chain is an alkylene group (preferably $C_1$–$C_{20}$, more preferably $C_1$–$C_{15}$), carbon chains which optionally include one or more double or triple bonds are also within the scope of the invention. Also included are carbon chains which include one or more substituents (such as hydroxyl, carboxylic acid or amide groups), and/or include one or more side chains or branches, selected from unsubstituted or substituted alkyl, alkenyl or alkynyl groups.

In some particularly preferred embodiments, the linking group is an ethylene, propylene, butylene, pentylene or decylene group.

Other lipophilic cations which may covalently be coupled to antioxidants in accordance with the present invention include the tribenzyl ammonium and phosphonium cations.

Preferred antioxidant compounds of the invention, including those of general formulae I and II as defined above, can be readily prepared, for example, by the following reaction:

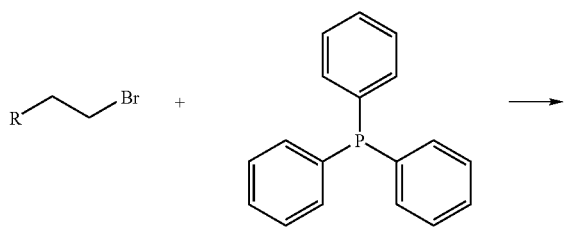

-continued

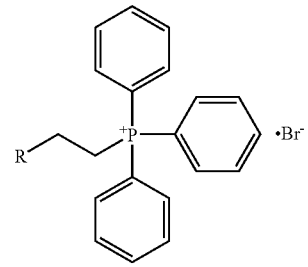

The general synthesis strategy is to heat a halogenated precursor, preferably a brominated or Iodinated precursor (RBr or RI) in an appropriate solvent with 2-3 equivalents of triphenylphosphine under argon for several days. The phosphonium compound is then isolated as its bromide or iodide salt. To do this the solvent is removed, the product is then triturated repeatedly with diethyl ether until an off-white solid remains. This is then dissolved in chloroform and precipitated with diethyl ether to remove the excess triphenylphosphine. This is repeated until the solid no longer dissolves in chloroform. At this point the product is recrystalised several times from methylene chloride/diethyl ether.

It will also be appreciated that the anion of the antioxidant compound thus prepared, which will be a halogen when this synthetic procedure is used, can readily be exchanged with another pharmaceutically or pharmacologically acceptable anion, if this is desirable or necessary, using ion exchange chromatography or other techniques known in the art.

The same general procedure can be used to make a wide range of mitochondrially targeted compounds with different antioxidant moieties R attached to the triphenylphosphonium (or other lipophilic cationic) salt. These will include a series of vitamin E derivatives, in which the length of the bridge linking the Vitamin-E function with the triphenylphosphonium salt is varied. Other antioxidants which can be used as R include chain breaking antioxidants, such as butylated hydroxyanisole, butylated hydroxytoluene, quinols (including those of formula II as defined above) and general radical scavengers such as derivatised fullerenes. In addition, spin traps, which react with free radicals to generate stable free radicals can also be synthesized. These will include derivatives of 5,5-dimethylpyrroline-N-oxide, tert-butylnitrosobenzene, tert-nitrosobenzene, α-phenyl-tert-butylnitrone and related compounds.

In some preferred embodiments of the invention, the antioxidant compound is a quinol derivative of the formula II defined above. A particularly preferred quinol derivative of the invention is the compound mitoquinol as defined above. Another preferred compound of the invention is a compound of formula II in which $(C)_n$ is $(CH_2)_5$, and the quinol moiety is the same as that of mitoquinol.

Once prepared, the antioxidant compound of the invention, in any pharmaceutically appropriate form and optionally including pharmaceutically-acceptable carriers or additives, will be administered to the patient requiring therapy and/or prophylaxis. Once administered, the compound will target the mitochondria within the cell.

Set out below are synthetic schemes which may be used to prepare some other specific mitochondrially targeted antioxidant compounds of the present invention, namely (1) a mitochondrially targeted version of buckminsterfullerene; (2) a mitochondrially targeted spin trap compound; and (3) a further synthetic route for a mitochondrially targeted spin trap compound.

Buckminsterfullerene Synthesis
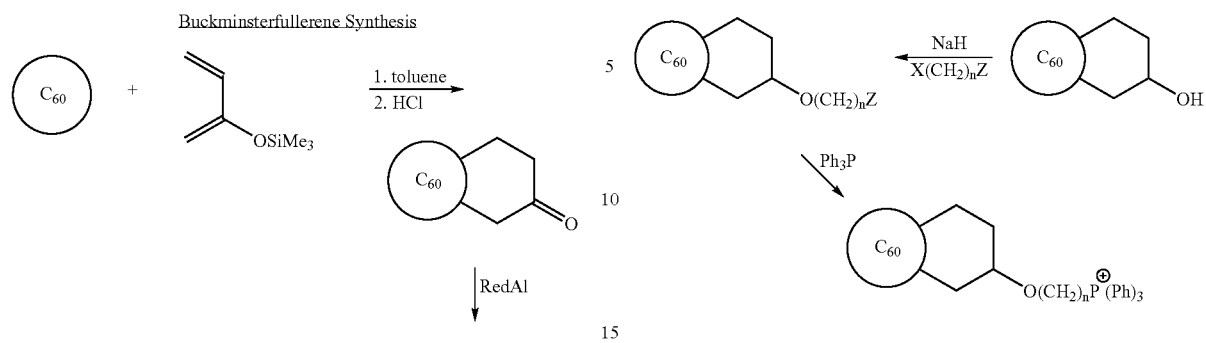
Spin Trap Synthesis I
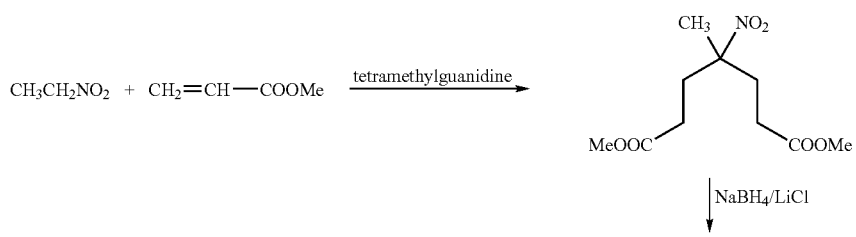
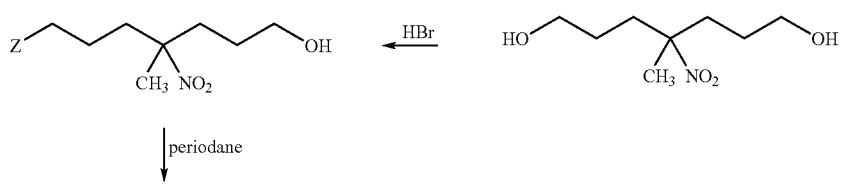
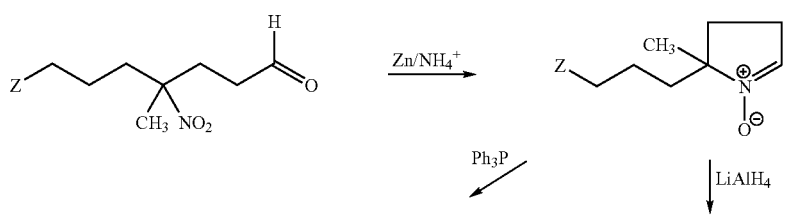
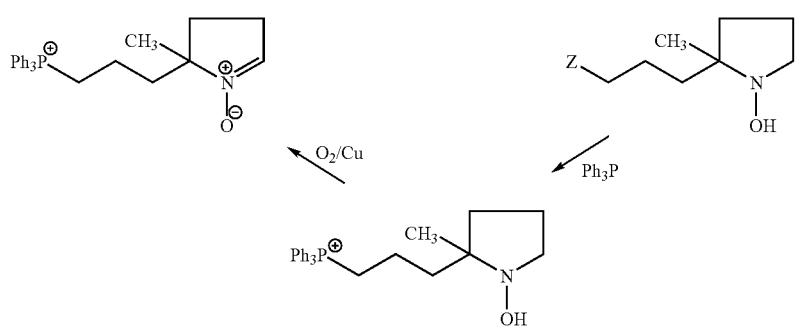

Spin Trap Synthesis II

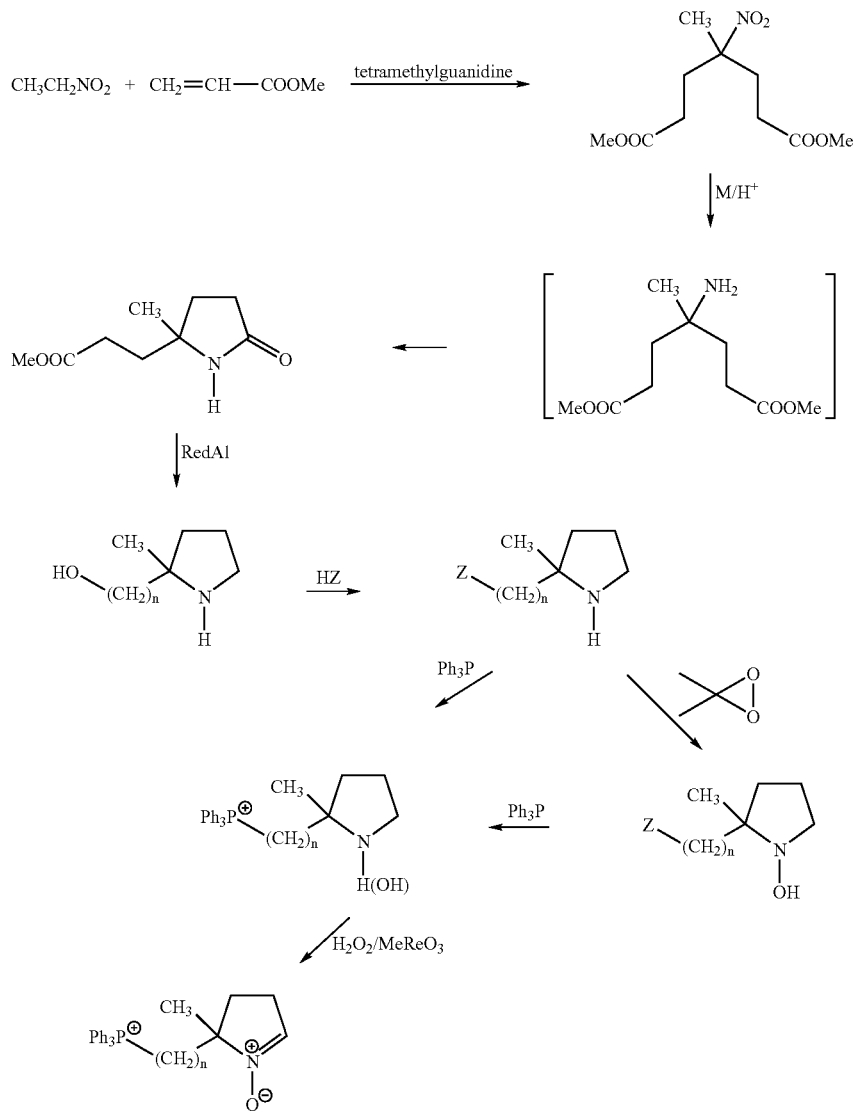

The invention will now be described in more detail with reference to the following non-limiting examples.

EXAMPLES

Example 1

Experimental

1. Synthesis of a Mitochondrially-targeted Vitamin-E Derivative (Compound 1)

The synthesis strategy for a mitochondrially-targeted vitamin-E derivative (compound 1) is as follows. The brominated precursor (compound 2) 2-(2-bromoethyl)-3,4-dihydro-6-hydroxy-2,5,7,8-tetramethyl-2H-1-benzopyran was synthesized by bromination of the corresponding alcohol as described by Grisar et al, (1995) (*J Med Chem* 38, 2880–2886). The alcohol was synthesized by reduction of the corresponding carboxylic acid as described by Cohen et al., (1979) (*J. Amer Chem Soc* 101, 6710–6716). The carboxylic acid derivative was synthesized as described by Cohen et al., (1982) (*Syn Commun* 12, 57–65) from 2,6-dihydroxy-2,5,7,8-tetramethylchroman, synthesized as described by Scott et al., (1974) (*J. Amer. Oil Chem. Soc.* 101, 6710–6716).

Compound 1

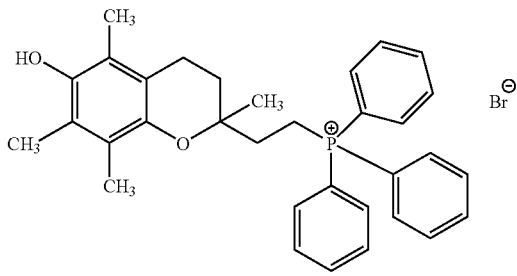

-continued

Compound 2

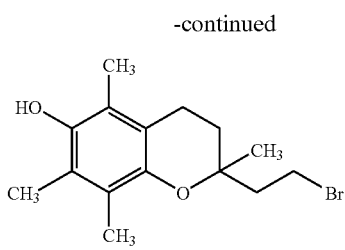

For the synthesis of compound 1, 1 g of compound 2 was added to 8 ml butanone containing 2.5 molar equivalents of triphenylphosphine and heated at 100° C. in a sealed Kimax tube under argon for 7–8 days. The solvent was removed under vacuum at room temperature, the yellow oil triturated with diethyl ether until an off-white solid remained. This was then dissolved in chloroform and precipitated with diethyl ether. This was repeated until the solid was insoluble in chloroform and it was then recrystalised several times from methylene chloride/diethyl ether and dried under vacuum to give a white hygroscopic powder.

2. Mitochondrial Uptake of Compound 1

To demonstrate that this targeting is effective, the exemplary vitamin E compound 1 was tested in relation to both isolated mitochondria and isolated cells. To do this a [$^3$H]-version of compound 1 was synthesized using [$^3$H]-triphenylphosphine and the mitochondrial accumulation of compound 1 quantitated by scintillation counting (FIG. 1) (Burns et al., 1995, *Arch Biochem Biophys* 332, 60–68; Burns and Murphy, 1997, *Arch Biochem Biophys* 339, 33–39). To do this rat liver mitochondria were incubated under conditions known to generate a mitochondrial membrane potential of about 180 mV (Burns et al., 1995; Burns and Murphy, 1997). Under these-conditions compound 1 was rapidly (<10 s) taken up into mitochondria with an accumulation ratio of about 6,000. This accumulation of compound 1 into mitochondria was blocked by addition of the uncoupler FCCP (carbonyl cyanide-p-trifluoromethoxyphenylhydrazone) which prevents mitochondria establishing a membrane potential (FIGS. 1 and 2) (Burns et al., 1995). Therefore compound 1 is rapidly and selectively accumulated into mitochondria driven by the mitochondrial membrane potential and this accumulation results in a concentration of the compound within mitochondria several thousand fold higher than in the external medium. This accumulation is rapidly (<10 s) reversed by addition of the uncoupler FCCP to dissipate the mitochondrial membrane potential after accumulation of compound 1 within the mitochondria. Therefore the mitochondrial specific accumulation is solely due to the mitochondrial membrane potential and is not due to specific binding or covalent interaction.

The mitochondrial specific accumulation of compound 1 also occurs in intact cells. This was measured as described by Burns and Murphy, 1997 and the accumulation was prevented by dissipating both the mitochondrial and plasma membrane potentials. In addition, compound 1 was not accumulated by cells containing defective mitochondria, which consequently do not have a mitochondrial membrane potential. Therefore the accumulation of compound 1 into cells is driven by the mitochondrial membrane potential.

Figure 2:
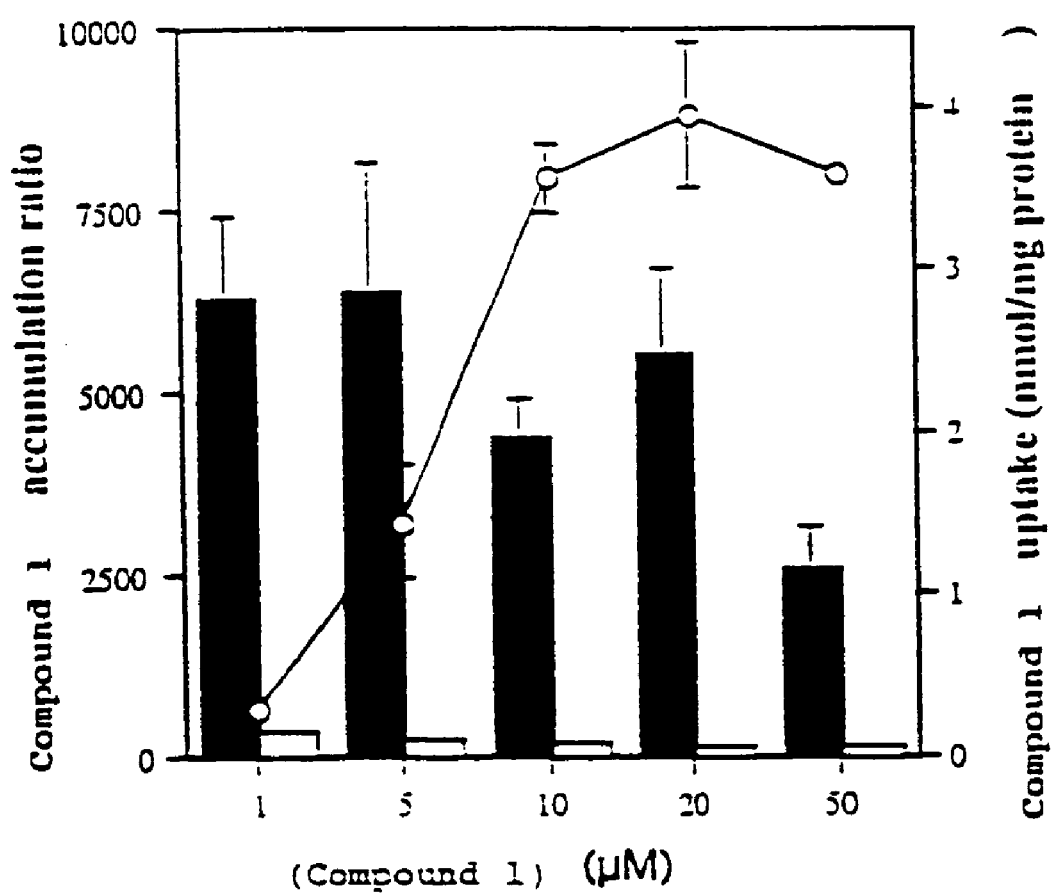
FIG. 2 is a graph which shows the accumulation of compound 1 by isolated mitochondria.
Figure 3:
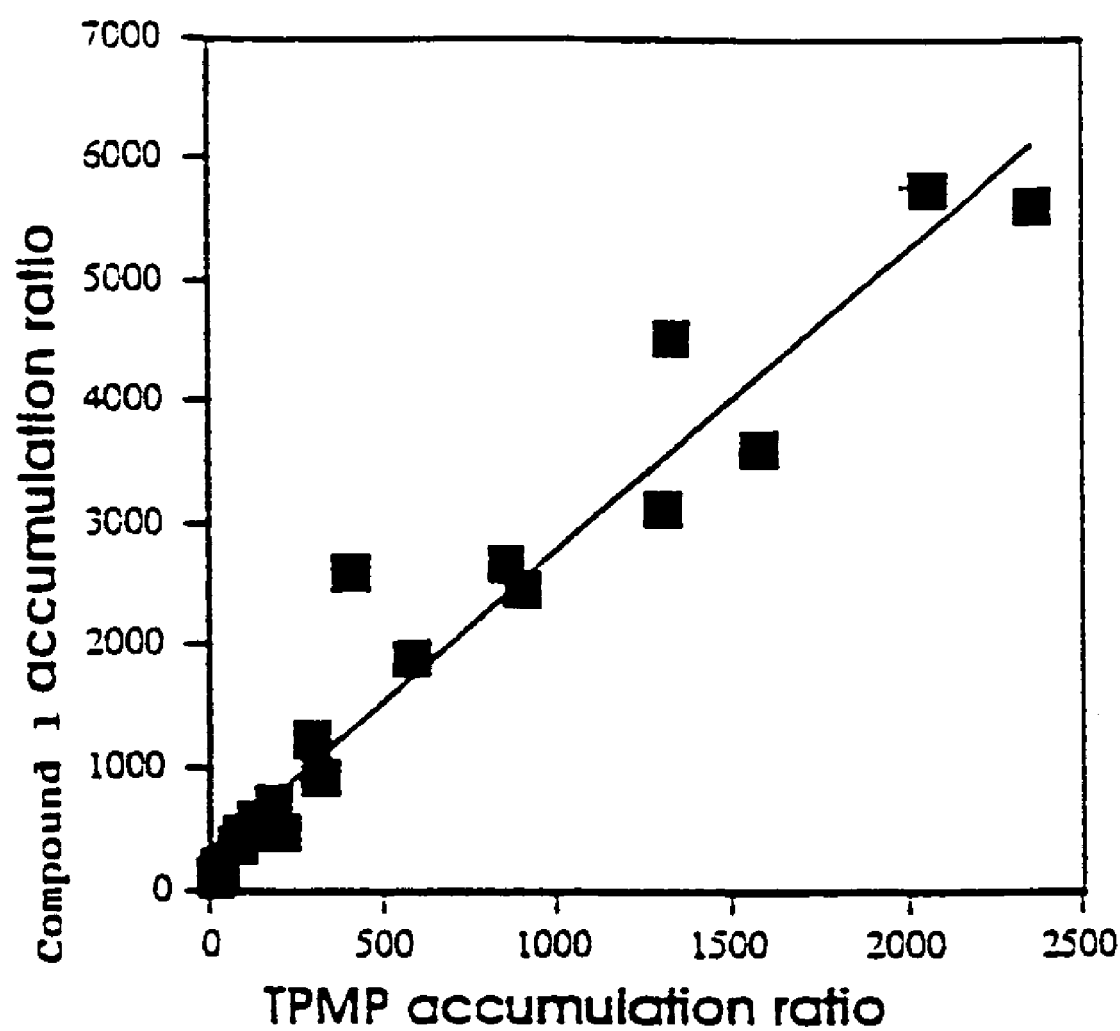
FIG. 3 is a graph which shows a comparison of a compound 1 uptake with that of the triphenylphosphonium cation (TPMP)

The accumulation ratio was similar across a range of concentrations of compound 1 and the amount of compound 1 taken inside the mitochondria corresponds to an intramitochondrial concentration of 4–8 mM (FIG. 2). This uptake was entirely due to the membrane potential and paralleled that of the simple triphenylphosphonium cation TPMP over a range of membrane potentials (FIG. 3). From comparison of the uptake of TPMP and compound 1 at the same membrane potential we infer that within mitochondria about 84% of compound 1 is membrane-bound (cf. About 60% for the less hydrophobic compound TPMP).

Further details of the experimental procedures and results are given below.

FIG. 1 shows the uptake of 10 μM [$^3$H] compound 1 by energised rat liver mitochondria (continuous line and filled symbols). The dotted line and open symbols show the effect of addition of 333 nM FCCP at 3 min. Incubation with FCCP from the start of the incubation led to the same uptake as for adding FCCP at 3 min (data not shown). Liver mitochondria were prepared from female Wistar rats by homogenisation followed by differential centrifugation in medium containing 250 mM sucrose, 10 mM Tris-HCL (pH 7.4) and 1 mM EGTA and the protein concentration determined by the biuret assay using BSA as a standard. To measure [$^3$H] compound 1 uptake mitochondria (2 mg protein/ml) were suspended at 25° C. in 0.5–1 ml 110 mM KCl, 40 mM Hepes-KOH, pH 7.2, 0.1 mM EDTA supplemented with nigericin (1 μg/ml), 10 mM succinate, rotenone 1.33 μg/ml and 60 nCi/ml [$^3$H] compound 1 and 10 μM compound 1. After the incubation mitochondria were pelleted by centrifugation and the [$^3$H] compound 1 in the supernatant and pellet quantitated by scintilation counting.

FIG. 2 shows the mitochondrial accumulation ratios [(compound 1/mg protein)/(compound 1/μl)] obtained following 3 min incubation of energised rat liver mitochondria with different concentrations of compound 1 (filled bars) and the effect of 333 nM FCCP on these (open bars). The dotted line and open circles show compound 1 uptake by mitochondria, corrected for FCCP-insensitive binding. To measure [3H] compound 1 accumulation ratio mitochondria (2 mg protein/ml)-were suspended at 25° C. in 0.5–1 ml 110 mM KCl, 40 mM Hepes-KOH, pH 7.2, 0.1 mM EDTA supplemented with nigericin (1 μg/ml), 10 mM succinate, rotenone 1.33 μg/ml and 6–60 nCi/ml [$^3$H] compound 1 and 1–50 μM compound 1. After the incubation mitochondria were pelleted by centrifugation and the [$^3$H] compound 1 in the supernatant and pellet quantitated by scintillation counting.

FIG. 3 shows a comparison of compound 1 uptake with that of TPMP at a range of mitochondrial membrane potentials. Energised rat liver mitochondria were incubated for 3 min with 10 μM compound 1 and 1 μM TPMP and different membrane potentials established with 0–8 mM malonate or 333 nM FCCP. The accumulation ratios of parallel incubations with either 60 nCi/ml [$^3$H] compound 1 or 50 nCi/ml [$^3$H] TPMP were determined, and the accumulation ratio for compound 1 is plotted relative to that of TPMP at the same membrane potential (slope=2.472, y intercept=319, r=0.97). Mitochondria (2 mg protein/ml) were suspended at 25° C. in 0.5–1 ml 110 mM KCl, 40 mM Hepes-KOH, pH 7.2, 0.1 mM EDTA supplemented with nigericin (1 μg/ml), 10 mM succinate, rotenone 1.33</ml.

3. Anti-Oxidant Efficacy of Compound 1

The compounds of the invention are also highly effective against oxidative stress. To demonstrate this, exemplary compound 1 was further tested using rat brain homogenates. The rat brain homogenates were incubated with or without various concentrations of the test compounds (compound 1; native Vitamin E (α-tocopherol), bromobutyl triphenylphosphonium bromide, Trolox (a water soluble form of Vitamin E) and compound 2, ie2-(2-bromoethyl)-3,4-dihydro-2,5,7,8-tetramethyl-2H-1-benzopyran-6-ol, the precursor of compound 1 ("Brom Vit E")) and the oxidative damage occurring over the incubation was quantitated using the TBARS assay (Stocks et al., 1974, *Clin Sci Mol Med* 47,215–222). From this the concentration of compound required to inhibit oxidative damage by 50% was determined. In this system 210 nM compound 1 inhibited oxidative stress by 50% while the corresponding value for native Vitamin E was 36 nM. The value for bromobutyltriphenylphosphonium bromide, which contains the triphenylphosphonium moiety but not the antioxidant Vitamin E moiety was 47 μM. These data show that compound 1 is an extremely effective antioxidant, within an order of magnitude as effective as Vitamin E. Comparison with bromobutyltriphenylphosphonium bromide shows that the antioxidant capability is due to the Vitamin E function and not to the phosphonium salt. Further details of the experimental procedures and results are set out below.

The $IC_{50}$ values for inhibition of lipid peroxidation were determined in rat brain homogenates, and are means±SEM or range of determinations on 2–3 brain preparations. Octan-1-ol/PBS partition coefficients are means±SEM for three independent determinations. N.D. not determined. Partition coefficients were determined by mixing 200 μM of the compound in 2 ml water-saturated octanol-1-ol with 2 ml octanol-saturated-PBS at room temperature for 1 h, then the two layers were separated by brief centrifugation and their concentrations determined spectrophotometrically from standard curves prepared in PBS or octanol. To measure antioxidant efficacy four rat brains were homogenised in 15 ml 40 mM potassium phosphate (pH 7.4), 140 mM NaCl at 4° C., particulate matter was pelleted (1,000×g at 4° C. for 15 min) and washed once and the combined supernatants stored frozen. Aliquots were rapidly thawed and 5 mg protein suspended in 800 μl PBS containing antioxidant or ethanol carrier and incubated at 37° C. for 30 min. Thiobarbituric acid reactive species (TBARS) were quantitated at 532 nm by adding 200 μl conc. $HClO_4$ and 200 μl 1% thiobarbituric acid to the incubation, heating at 100° C. for 15 min and then cooling and clarification by centrifugation (10,000×g for 2 min). The results are shown in Table 1 below.

TABLE 1

Partition coefficients and antioxidant efficacy of compound 1 and related compounds

| Compound | $IC_{50}$ for inhibition of lipid peroxidation (nM) | Octanol:PBS partition coefficient |
|---|---|---|
| Compound 1 | 210 ± 58 | 7.37 ± 1.56 |
| Bromo Vit E | 45 ± 26 | 33.1 ± 4.4 |
| α-Tocopherol | 36 ± 22 | 27.4 ± 1.0 |
| Trolox | 18500 ± 5900 | N.D. |
| BrBTP | 47000 ± 13000 | 3.83 ± 0.22 |

Figure 4:
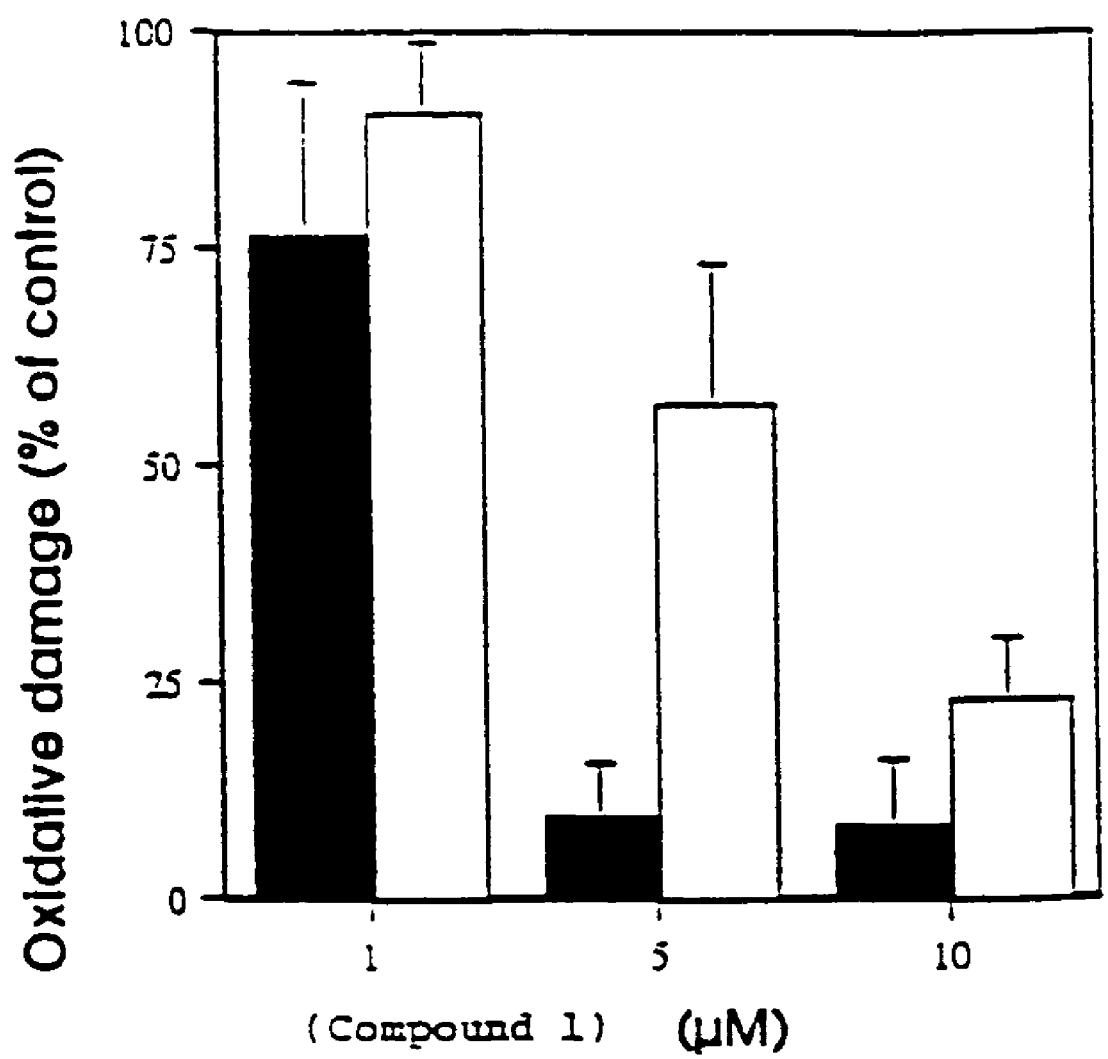
FIG. 4 is a graph which shows that compound 1 protects mitochondria against oxidative damage.
Figure 5:
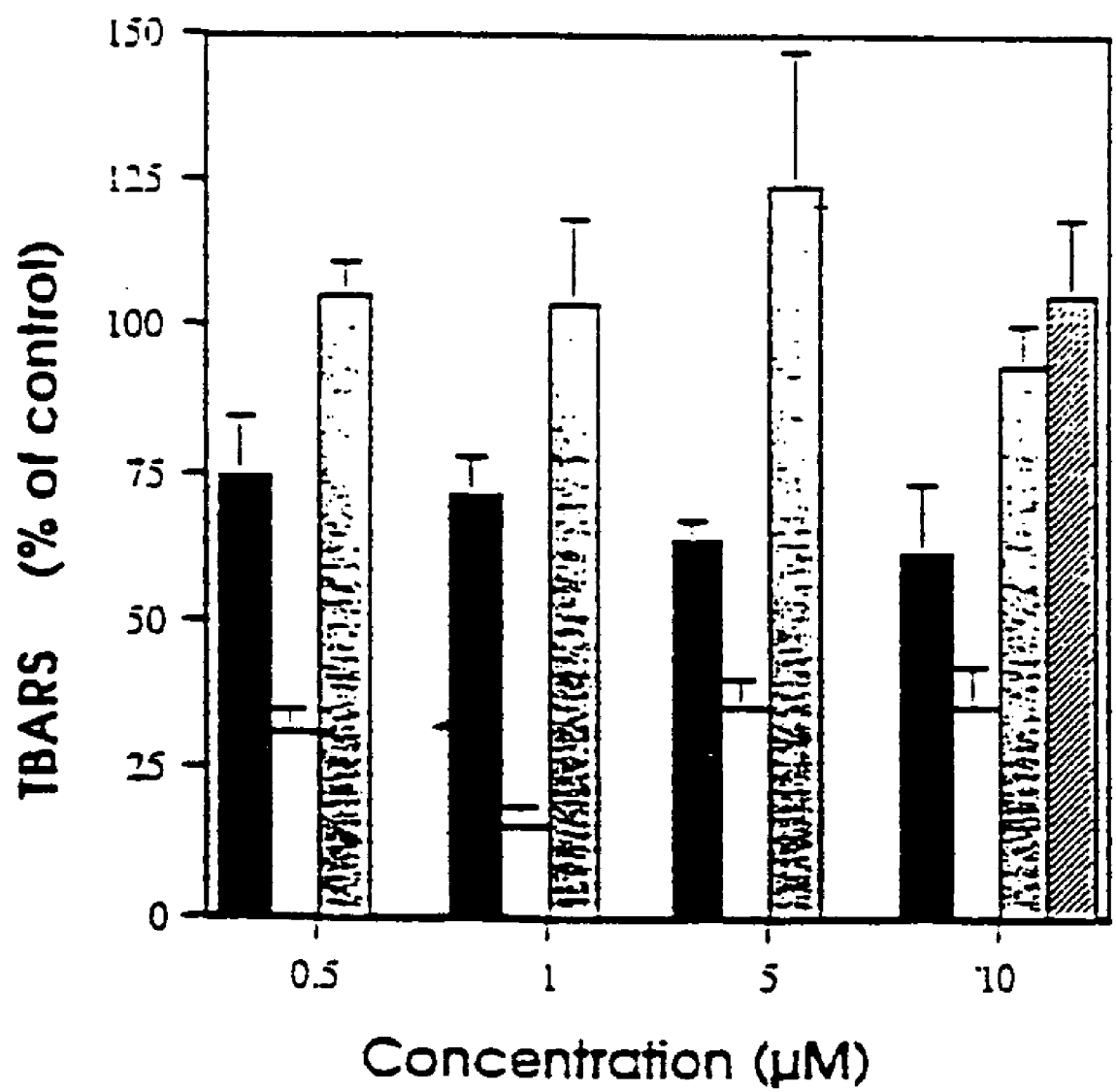
FIG. 5 is a graph which compares compound 1 with vitamin E and the effect of uncoupler and other lipophilic cations.
Figure 6:
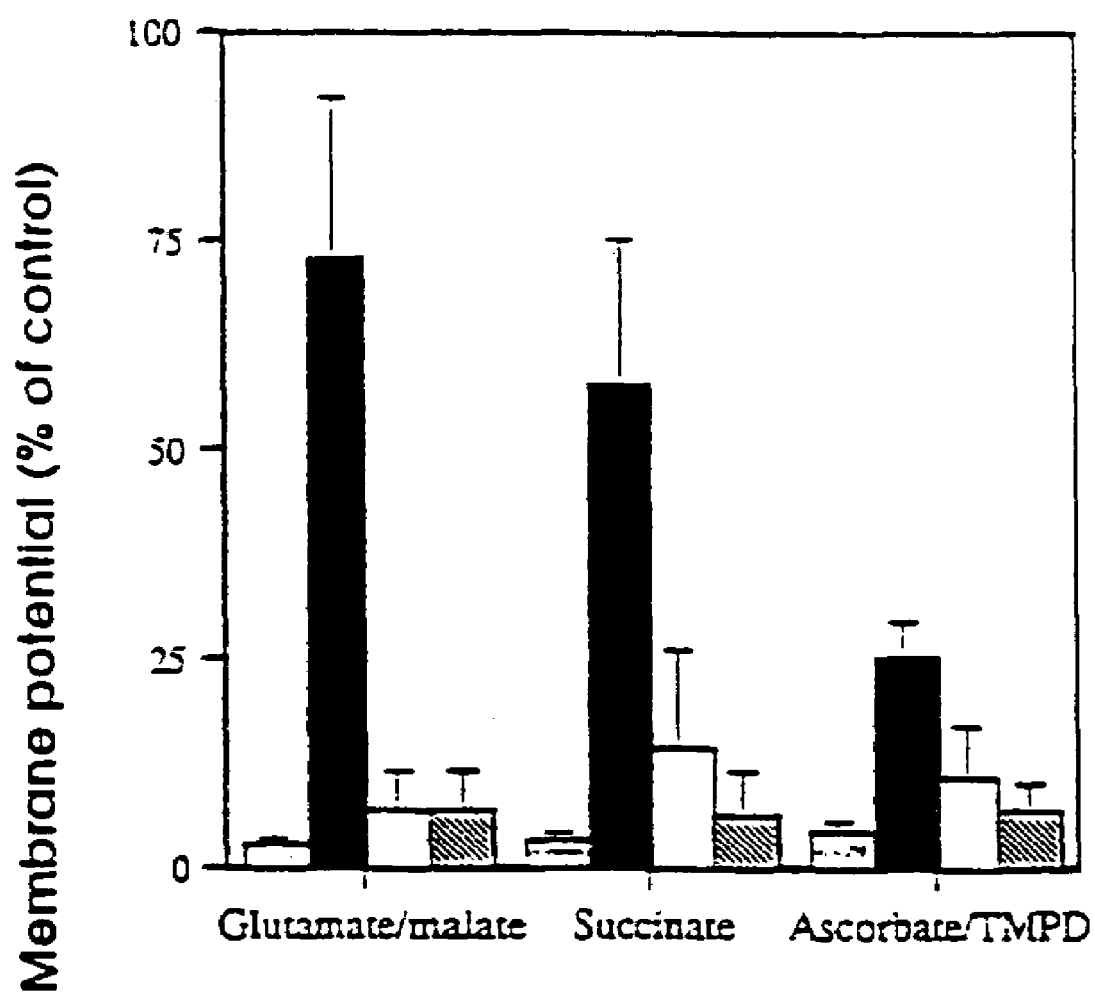
FIG. 6 is a graph which shows that compound 1 protects mitochondrial function from oxidative damage.
Figure 7:
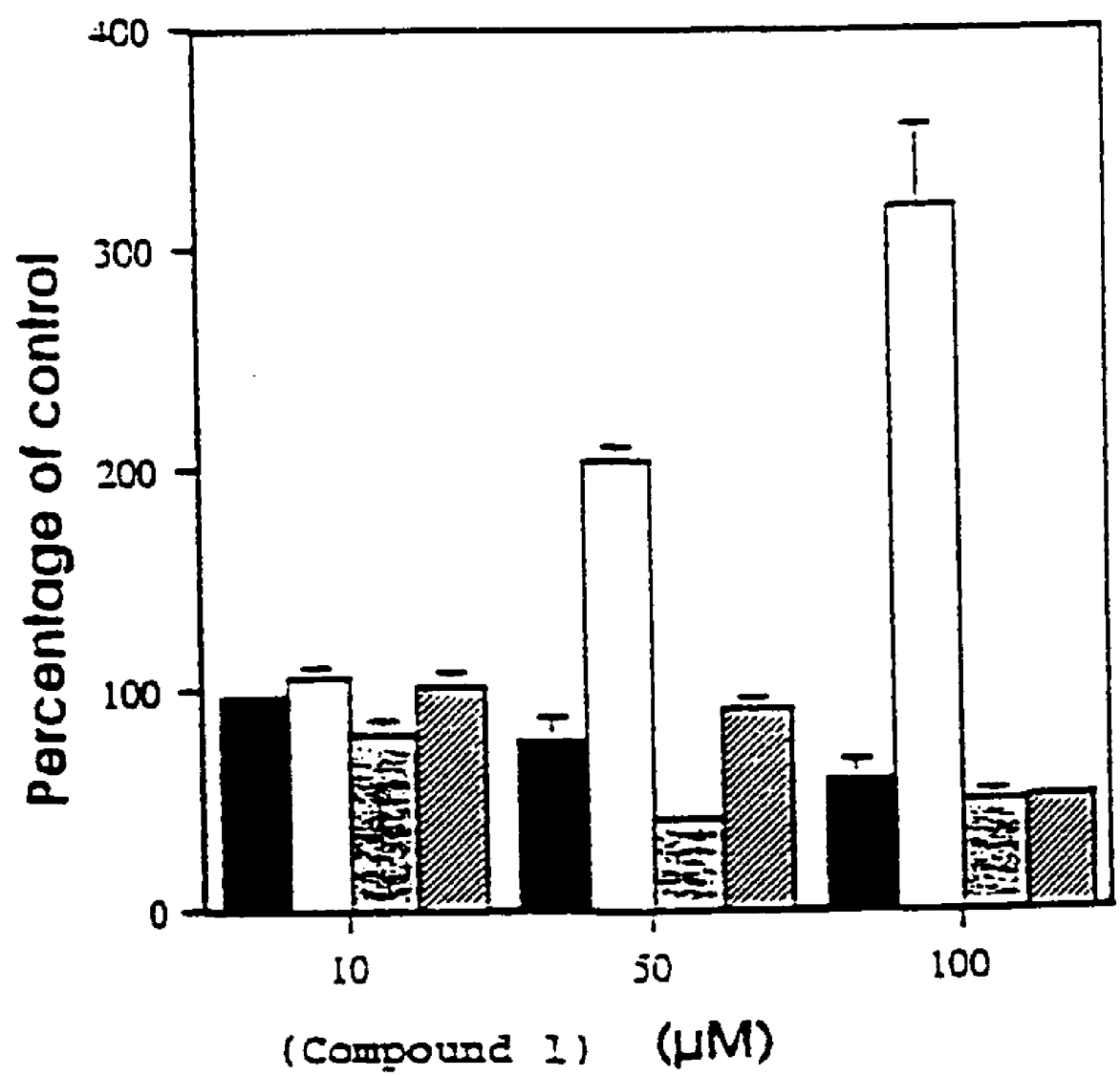
FIG. 7 is a graph which shows the effect of compound 1 on mitochondrial function.

When mitochondria were exposed to oxidative stress compound 1 protected them against oxidative damage, measured by lipid peroxidation and protein carbonyl formation (FIG. 4). This antioxidant protection was prevented by incubating mitochondria with the uncoupler FCCP to prevent uptake of compound 1, and lipophilic cations alone did not protect mitochondria (FIG. 5). Most importantly, the uptake of compound 1 protected mitochondrial function, measured by the ability to generate a membrane potential, far more effectively than Vitamin E itself (FIG. 6). This shows that the accumulation of compound 1 into mitochondria selectively protects their function from oxidative damage. In addition, we showed that compound 1 is not damaging to mitochondria at the concentrations that afford protection (FIG. 7).

Figure 9:
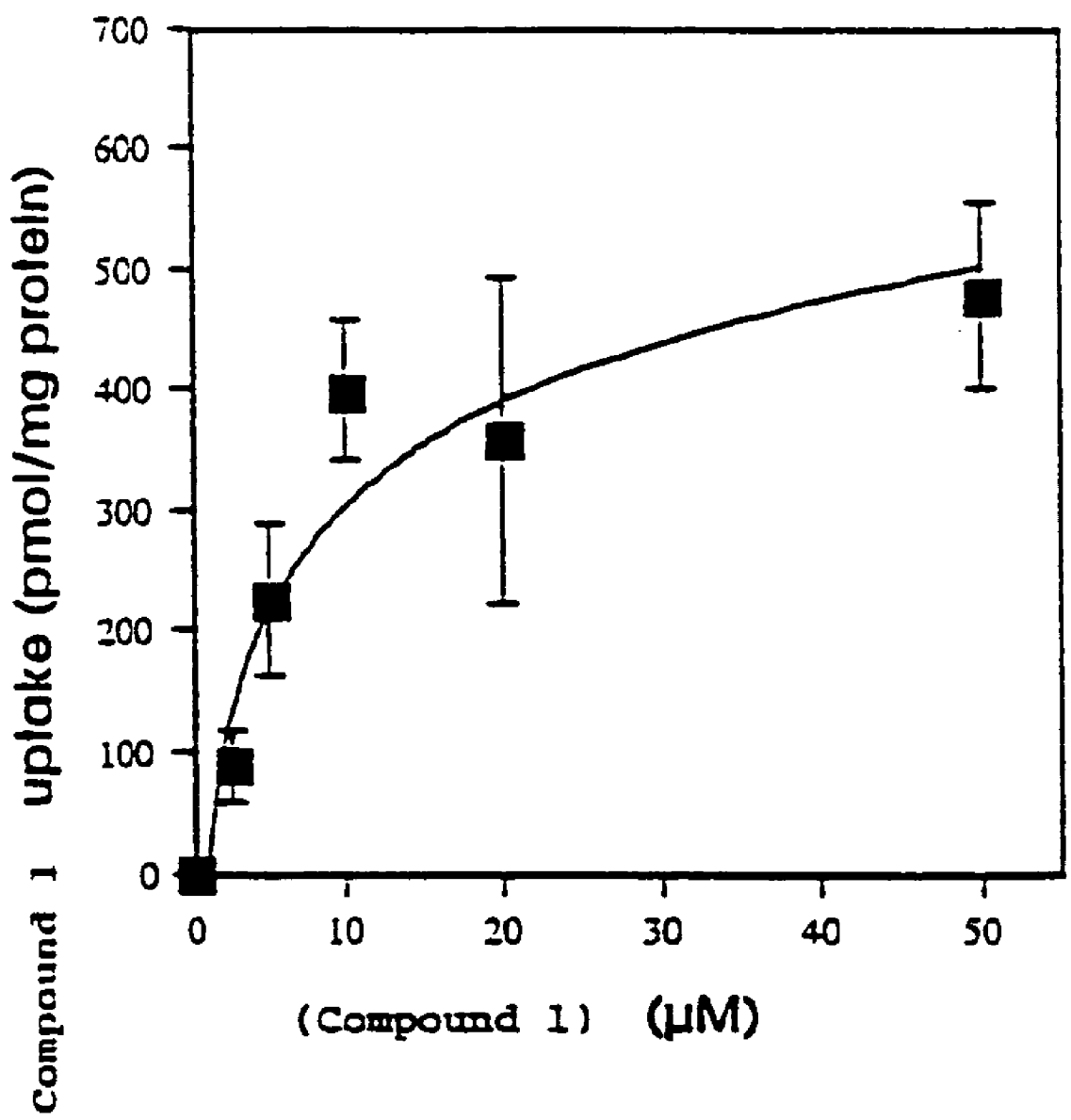
FIG. 9 is a graph which shows the energisation-sensitive uptake of compound 1 by cells.
Figure 10:
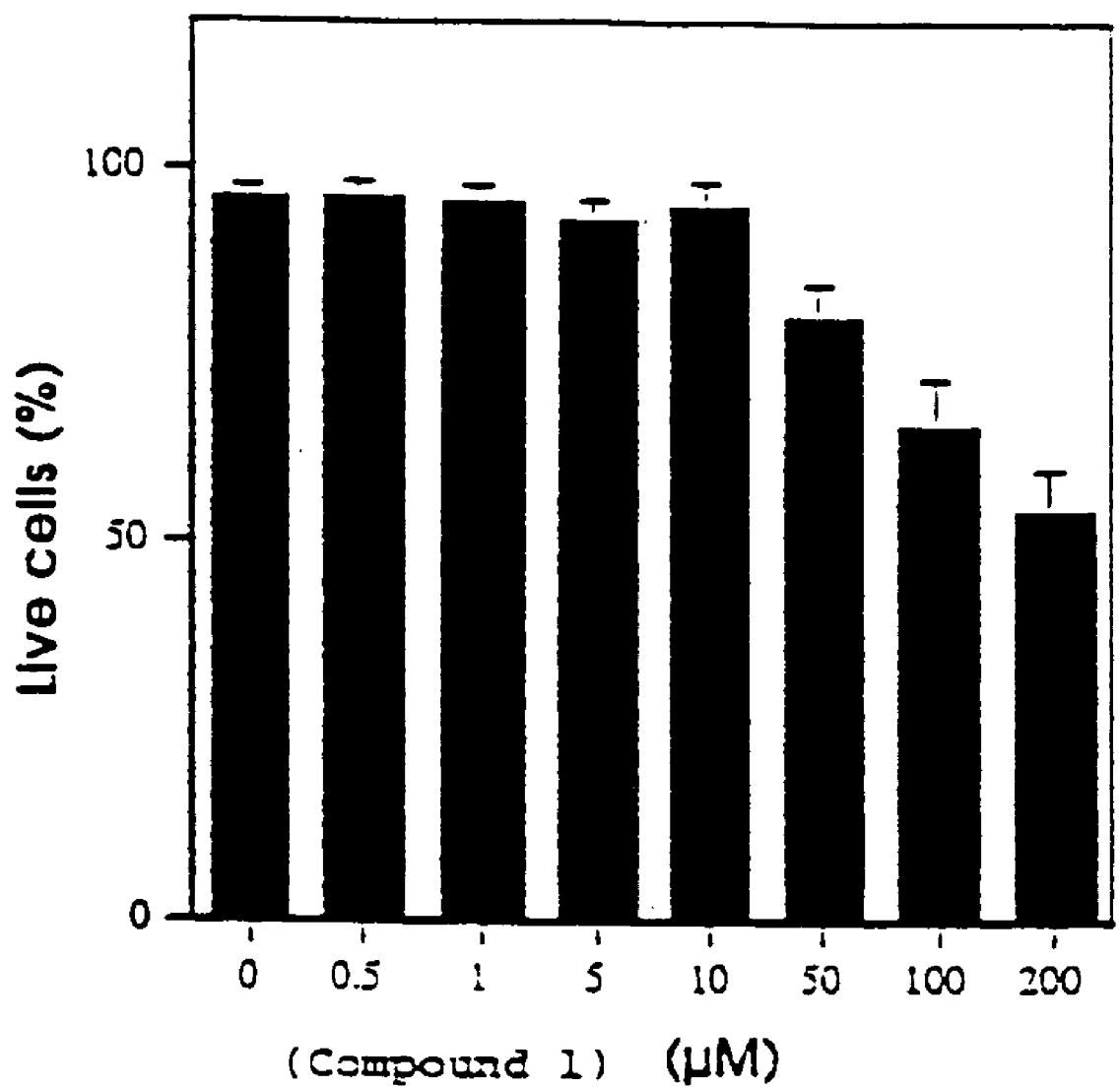
FIG. 10 is a graph which shows the effect of compound 1 on cell viability.

The next step was to determine whether compound 1 was accumulated by intact cells. Compound 1 was rapidly accumulated by intact 143B cells, and the amount accumulated was greater than that by ρ° cells derived from 143B cells. This is important because the ρ° cells lack mitochondrial DNA and consequently have far lower mitochondrial membrane potential than the 143B cells, but are identical in every other way, including plasma membrane potential, cell volume and protein content (FIG. 8); this suggests that most of the compound 1 within cells is mitochondrial. A proportion of this uptake of compound 1 into cells was inhibited by blocking the plasma and mitochondrial membrane potentials (FIG. 9). This energisation-sensitive uptake corresponds to an intra mitochondrial concentration of compound 1 of about 2–4 mM, which is sufficient to protect mitochondria from oxidative damage. These concentrations of compound 1 are not toxic to cells (FIG. 10).

Further details of the experimental procedures and results are discussed below.

FIG. 4 shows the protection of mitochondria against oxidative damage by compound 1. Mitochondria were exposed to oxidative stress by incubation with iron/ascorbate and the effect of compound 1 on oxidative damage assessed by measuring TBARS (filled bars) and protein carbonyls (open bars). Rat liver mitochondria (10 mg protein) were incubated at 25° C. in a shaking water bath in 2 ml medium containing 100 mM KCl, 10 mM Tris, pH 7.7, supplemented with rotenone (1.33 μg/ml), 10 mM succinate, 500 μM ascorbate and other additions. After preincubation for 5 min, 100 μM $FeSO_4$ was added and 45–55 min later duplicate samples were removed and assayed for TBARS or protein carbonyls.

FIG. 5 shows a comparison of compound 1 with vitamin E and the effect of uncoupler and other lipophilic cations. Energised rat liver mitochondria were exposed to tert-butylhydroperoxide and the effect of compound 1 (filled bars), α-tocopherol (open bars), compound 1+333 nM FCCP (stippled bars) or the simple lipophilic cation bromobutyl triphenylphosphonium (cross hatched bars) on TBARS formation determined. Rat liver mitochondria (4 mg protein) were incubated in 2 ml medium containing 120 mM KCl, 10 mM Hepes-HCl pH 7.2; 1 mM EGTA at 37° C. in a shaking water bath for 5 min with various additions, then tert butyl hydroperoxide (5 mM) was added, and the mitochondria incubated for a further 45 min and then TBARS determined.

FIG. 6 shows how compound 1 protects mitochondrial function from oxidative damage. Energised rat liver mitochondria were incubated with iron/ascorbate with no additions (stippled bars), 5 μM compound 1 (filled bars), 5 μM α-tocopherol. (open bars) or 5 μM TPMP (cross hatched bars), and then isolated and the membrane potential generated by respiratory substrates measured relative to control incubations in the absence of iron/ascorbate. Rat liver mitochondria were incubated at 25° C. in a shaking water bath in 2 ml medium containing 100 mM KCl, 10 mM Tris, pH 7.7, supplemented with rotenone (1.33 μg/ml), 10 mM succinate, 500 μM ascorbate and other additions. After preincubation for 5 min, 100 μM $FeSO_4$ was added and after 30 min the incubation was diluted with 6 ml ice-cold STE 250 mM sucrose, 10 mM Tris-HCL (pH 7.4) and 1 mM EGTA, pelleted by centrifugation (5 min at 5,000×g) and the pellet resuspended in 200 μl STE and 20 μl (=1 mg protein) suspended in 1 ml 110 mM KCl, 40 mM HEPES, 0.1 M EDTA pH 7.2 containing 1 μM TPMP and 50 nCi/ml [$^3$H] TPMP either 10 mM glutamate and malate, 10 mM succinate and rotenone, or 5 mM ascorbate/100 μM TMPD with rotenone and myxothiazol (2 μg/ml), incubated at 25° C. for 3 min then pelleted and the membrane potential determined as above and compared with an incubation that had not been exposed to oxidative stress.

FIG. 7 shows the effect of compound 1 on the membrane potential (filled bars) and respiration rate of coupled (open bars), phosphorylating (stippled bars) and uncoupled mitochondria (cross hatched bars), as a percentage of values in the absence of compound 1. The effect of various concentrations of compound 1 on the membrane potential of isolated mitochondria was determined from the distribution of [$^3$H] TPMP by incubating rat liver mitochondria (2 mg protein/ml) in 0.5 ml medium as above containing 1 μM TPMP and 50 nCi/ml [$^3$H] TPMP at 25° C. for 3 min. After the incubation mitochondria were pelleted by centrifugation and the [$^3$H] TPMP in the supernatant and pellet quantitated by scintillation counting and the membrane potential calculated assuming a volume of 0.5 μl/mg proteins and that 60% of intramitochondrial TPMP is membrane bound. To measure the effect of compound 1 on coupled, phosphorylating and uncoupled respiration rates, mitochondria (2 mg protein/ml) were suspended in 120 mM KCl, 10 mM Hepes-HCl pH 7.2, 1 mM EGTA, 10 mM K Pi in a 3 ml Clark oxygen electrode then respiratory substrate, ADP (200 μM) and FCCP (333 nM) were added sequentially to the electrode and respiration rates measured.

Figure 8:
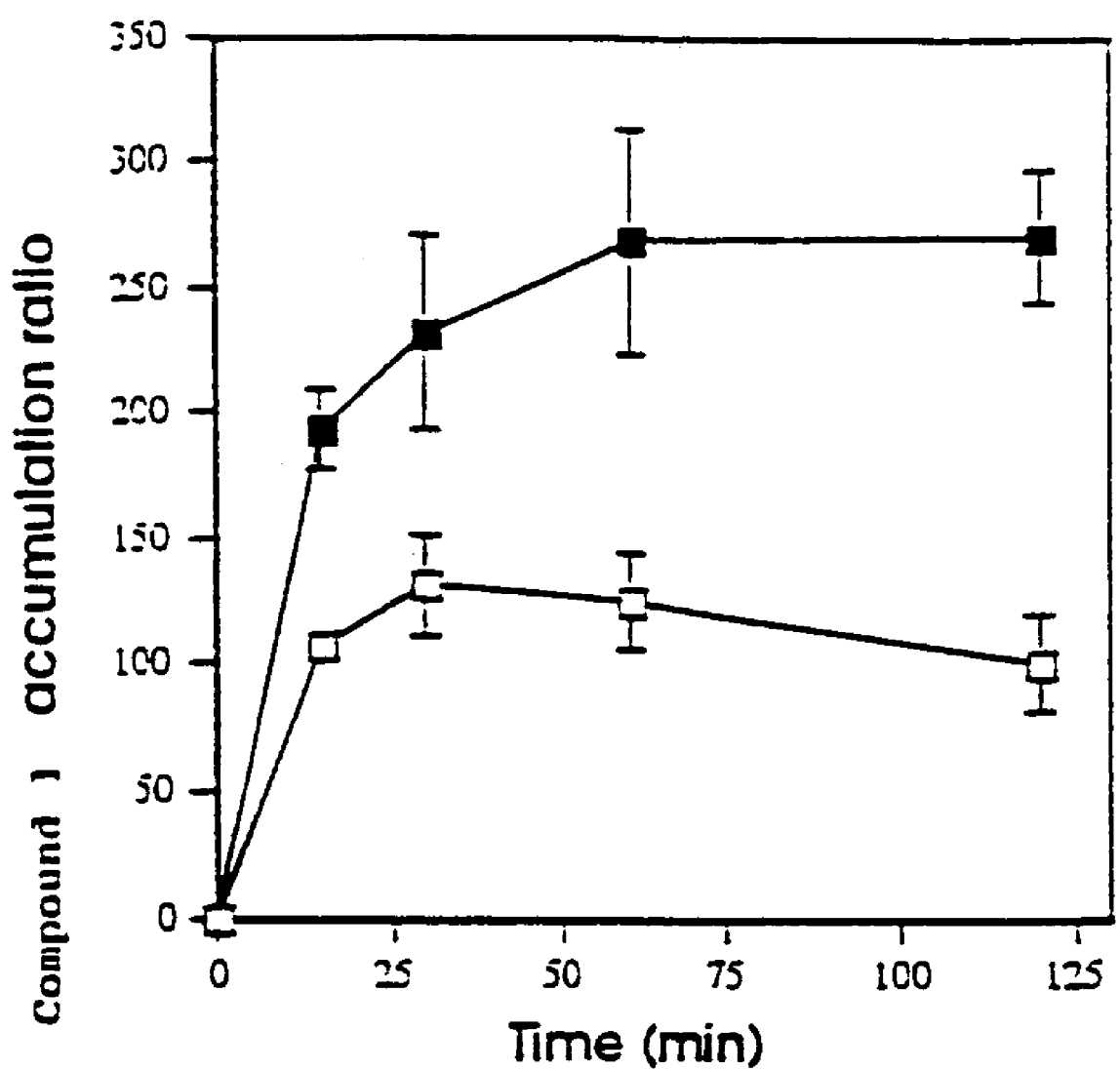
FIG. 8 is a graph which shows the uptake of compound 1 by cells.

FIG. 8 shows the uptake of compound 1 by cells. Here $10^6$ 143B cells (closed symbols) or ρ° cells (open symbols) were incubated with 1 μM [3H] compound 1 and the compound 1 accumulation ratio determined. Human osteosarcoma 143B cells and a derived ρ° cell line lacking mitochondrial DNA were cultured in DMEM/10% FCS (foetal calf serum) supplemented with uridine and pyruvate under an atmosphere of 5% $CO_2$/95% air at 37° C., grown to confluence and harvested for experiments by treatment with trypsin. To measure [$^3$H] compound 1 accumulation cells ($10^6$) were incubated in 1 ml HEPES-buffered DMEM. At the end of the incubation, cells were pelleted by centrifugation, the cell pellet and the supernatant prepared for scintillation counting and the accumulation ratio [compound 1/mg protein]/(compound 1/μl)]calculated.

FIG. 9 shows the amount of compound 1 taken up by $10^6$ 143B cells over 1 h incubation, corrected for inhibitor-insensitive binding. Human osteosarcoma 143B cells were incubated in 1 ml HEPES-buffered DMEM with 1-50 μM compound 1 supplemented with 6–60 nCi/ml [$^3$H] compound 1. To determine the energistration-dependent uptake, parallel incubations with 12.5 μM oligomycin, 20 μM FCCP; 10 μM myxathiazol. 100 nM valinomycin and 1 mM ouabain were carried out. At the end of the incubation, cells were pelleted by centrifugation and prepared for scintillation counting and the energisation-sensitive uptake determined.

FIG. 10 shows the effect of compound 1 on cell viability. Here, confluent 143B cells in 24 well tissue culture dishes were incubated with various concentrations of compound 1 for 24 h and cell viability measured by lactate dehydrogenase release.

Example 2

Synthesis of [10-(6'-ubiquinolyl)decyltriphenylphosphonium bromide] (Herein Referred to as "Mitoquinol")

Synthesis of Precursors

To synthesise 11-bromoundecanoic peroxide 11-bromoundecanoic acid (4.00 g, 15.1 mmol) and $SOCl_2$ (1.6 mL, 21.5 mmol) were heated, with stirring, at 90° C. for 15 min. Excess $SOCl_2$ was removed by distillation under reduced pressure (15 mm Hg, 90° C.) and the residue (IR, 1799 cm$^{-1}$) was dissolved in diethyl ether (20 mL) and the solution cooled to 0° C. Hydrogen peroxide (30%, 1.8 mL) was added, followed by dropwise addition of pyridine (1.4 mL) over 45 min. Diethyl ether (10 mL) was added and the mixture was stirred for 1 h at room temperature then diluted with diethyl ether (150 mL) and washed with $H_2O$ (2×70 mL), 1.2 M HCl (2×70 mL), $H_2O$ (70 mL), 0.5 M $NaHCO_3$ (2×70 mL) and $H_2O$ (70 mL). The organic phase was dried over $MgSO_4$ and the solvent removed at room temperature under reduced pressure, giving a white solid (3.51 g). IR (nujol mull) 1810, 1782.

6-(10-bromodecyl)ubiquinone was synthesised by mixing crude material above (3.51 g, 12.5 mmol max), (ubiquinoneo, 1.31 g, 7.19 mmol, Aldrich) and acetic acid (60 mL) and stirring the mixture for 20 h at 100° C. The mixture was diluted with diethyl ether (600 mL) and washed with $H_2O$ (2×400 mL), 1M HCl (2×450 mL), 0.50 M $NaHCO_3$ (2×450 mL) and $H_2O$ (2×400 mL). The organic phase was dried over $MgSO_4$. The solvent was removed under reduced pressure, giving a reddish solid (4.31 g). Column chromatography of the crude solid on silica gel (packed in $CH_2Cl_2$) and elution with $CH_2Cl_2$ gave the product as a red oil (809 mg, 28%) and unreacted ubiquinone as a red solid (300 mg, 1.6 mmol, 13%). TLC: $R_f$ ($CH_2Cl_2$, diethyl ether 20:1) 0.46; IR (neat) 2928, 2854, 1650, 1611, 1456, 1288; $\lambda_{max}$ (ethanol): 278 nm; $^1$H NMR (299.9 MHz) 3.99 (s, 6H, 2×—$OCH_3$), 3.41 (t, J=6.8 Hz, 3H, —$CH_2$—Br), 2.45 (t, J=7.7 Hz, 2H, ubquinone-$CH_2$—), 2.02, (s, 3H, —$CH_3$), 1.89 (quin, J=7.4 Hz, 3H, —$CH_2$ —$CH_2$—Br), 1.42–1.28 (m, 20H, —($CH_2$)$_7$—); $^{13}$C NMR (125.7 MHz) 184.7 (carbonyl), 184.2 (carbonyl), 144.3 (2C, ring), 143.1 (ring), 138.7 (ring), 61.2 (2×—$OCH_3$), 34.0 (—$CH_2$—), 32.8 (—$CH_2$—), 29.8(—$CH_2$—), 29.4 (2×—$CH_2$ —), 29.3 (—$CH_2$—), 28.7 (2×—$CH_2$ —), 28.2 (—$CH_2$—), 26.4(—$CH_2$—), 11.9(—$CH_3$). Anal. Calcd. For $C_{19}H_{29}O_2Br$:C, 56.86; H, 7.28; Found: C, 56.49, H, 7.34; LREI mass spectrum: calcd. For $C_{19}H_{29}O_2Br$ 400/402; Found 400/402.

To form the quinol, 6-(10-bromodecyl)-ubiquinol, $NABH_4$ (295 mg, 7.80 mmol) was added to a solution of the quinone (649 mg, 1.62 mmol) in methanol (6 mL) and stirred under argon for 10 min. Excess $NaBH_4$ was quenched with 5% HCl (2 mL) and the mixture diluted with diethyl ether (40 mL). The organic phase was washed with 1.2 M HCl (40 mL) and saturated NaCl (2×40 mL), and dried over $MgSO_4$. The solvent was removed under reduced pressure, giving a yellow oily solid (541 mg, 83%). $^1$H NMR (299.9 MHz) 5.31 (s, 1H, —OH), 5.26 (s, 1H, —OH), 3.89 (s, 6H, 2×—$OCH_3$), 3.41(t, J=6.8 Hz, 2H, —$CH_2$—Br), 2.59 (t, J=7.7 Hz, 2H ubquinol-$CH_2$—), 2.15 (s, 3H, $CH_3$) 1.85 (quin, J=7.4 Hz, 2H, —$CH_2$—$CH_2$—Br), 1.44–1.21 (m, 19H, —$CH_2$)$_7$—).

Synthesis of
10-(6'-ubiquinolyl)decyltriphenylphosphonium bromide ('mitoquinol')

To synthesise 10-(6'-ubiquinolyl)decyltriphenylphosphonium bromide. To a 15 mL Kimax tube were added 6-(10-bromodecyl)ubiquinol (541 mg, 1.34 mmol), $PPH_3$ (387 mg, 1.48 mmol), ethanol (95%, 2.5 mL) and a stirring bar. The tube was purged with argon, sealed and the mixture stirred in the dark for 88 h at 85° C. The solvent was removed under reduced pressure, giving an oily orange residue. The residue was dissolved in $CH_2Cl_2$ (2 mL) followed by addition of pentane (20 mL). The resultant suspension was refluxed for 5 min at 50° C. and the supernatant decanted. The residue was dissolved in $CH_2Cl_2$ (2 mL) followed by addition of diethyl either (20 mL). The resultant suspension was refluxed for 5 min at 40° C. and the supernatant decanted. The $CH_2Cl_2$/diethyl ether reflux was repeated twice more. Residual solvent was removed under reduced pressure, giving crude product as a cream solid (507 mg). $^1$H NMR (299.9 MHz) 7.9–7.6 (m, 20H, —P$^-$ Ph$_3$), 3.89 (s, 6H, 2×—OCH$_3$), 3.91–3.77(m, 2—H, CH$_2$—P$^+$Ph$_3$), 2.57 (t, J=7.8 Hz, 2H ubquinol—CH$_2$—), 2.14 (s, 3H, CH$_3$), 1.6–1.2 (m, 23H, —(CH$_2$)$_8$—). $^{31}$P NMR (121.4 MHz) 25.1.

The crude product (200 mg) was oxidized to 10-(6'-ubiquinonyl)decyltriphenylphosphonium bromide (the oxidised form) by stirring in CDCl$_3$ under an oxygen atmosphere for 13 days. The oxidation was monitored by $^1$H NMR and was complete after 13 days. The solvent was removed under reduced pressure and the resultant residue dissolved in $CH_2Cl_2$ (5 mL). Excess diethyl ether (15 mL) was added and the resultant suspension stirred for 5 min. The supernatant was decanted and the $CH_2Cl_2$/diethyl ether precipitation repeated twice more. Residual solvent was removed under reduced pressure, giving crude product as a brown sticky solid (173 mg).

The quinone was reduced to the quinol by taking a mixture of crude quinone and quinol (73 mg, ca. 3:1 by 1H NMR) in methanol (1 mL) was added NaBH$_4$ (21 mg, 0.55 mmol). The mixture was stirred slowly under an argon atmosphere for 10 min. Excess NABH$_4$ was quenched with 5% HBr (0.2 mL) and the mixture extracted with $CH_2Cl_2$. The organic extract was washed with H$_2$O (3×5 mL). Solvent was removed under reduced pressure, giving a mixture of quinone and quinol (ca 1:5 by $^1$H NMR) as a pale yellow solid (55 mg). For routine preparation of the quinol form the ethanolic solution, dissolve in 5 vols of water, (=1 ml) add a pinch of NaBH4 leave on ice in the dark for 5 min, then extract 3×0.5 ml dichloromethane, Wash with water/HCl etc blow off in nitrogen, dissolve in same vol of etoh and take spectrum and store at −80 under argon. Yield about 70–80%. Oxidises rapidly in air so should be prepared fresh. vortex with 1 ml 2M NaCl. Collect the upper organic phase and evaporate to dryness under a stream of N$_2$ and dissolve in 1 ml ethanol acidified to pH 2.

Synthesis of [$^3$H]-10-(6'-ubiquinonyl)decyltriphenylphosphonium bromide

To a Kimax tube was added 6-(10-bromodecyl)ubiquinol (6.3 mg; 15.6 mmol) triphenylphosphine (4.09 mg; 15.6 mmol) and 100 μl ethanol containing [$^3$H] triphenylphosphine (74 μCi custom synthesis by Moravek Biochemicals, Brea, Calif., USA, Spec Ac 1 Ci/mmol) and 150 μl ethanol added. The mixture was stirred in the dark under argon for 55 h at 80° C. Then it was cooled and precipitated by adition of 5 ml diethyl ether. The orange solid was dissolved in few drops of dichloromethane and then precipitated with diethyl ether and the solid was washed (×4) with ~2 ml diethyl ether. Then dissolved in ethanol to give a stock solution of 404 μM which was stored at −20° C. The UV absorption spectrum and TLC were identical to those of the unlabelled 10-(6'-ubiquinonyl)decyltriphenylphosphonium bromide and the specific activity of the stock solution was 2.6 mCi/mmol.

Extinction Coefficients

Stock solutions of the quinone in ethanol were stored at −80° C. in the dark and their concentrations confirmed by 31P nmr. The compound was converted to the fully oxidised form by incubation in basic 95% ethanol over an hour on ice or by incubation with beef heart mitochondrial membrane at room temperature, either procedure leading to the same extinction coefficient of 10,400 M$^{-1}$ cm$^{-1}$ at the local maximum of 275 nm, with shoulders at 263 and 268 nm corresponding to the absorption maxima of the triphenylphosphonium moiety (Smith et al, *Eur. J. Biochem.*, 263, 709–716, 1999; Burns et al, *Archives of Biochemistry and Biophysics*, 322, 60–68, 1995) and a broad shoulder at 290 nm due to the quinol (Crane et al, *Meth Enzymol.*, 18C, 137–165, 1971). Reduction by addition of NaBH4 gave the spectrum of the quinol which had the expected peak at 290 nm with an extinction coefficient of 1800 M$^{-1}$ cm$^{-1}$ and the extinction coefficient for at 268 nm was 3,000 M$^{-1}$ cm$^{-1}$ the same as that for the phosphonium moiety alone (Burns, 1995 above). The extinction coefficient of 10,400 M$^{-1}$ cm$^{-1}$ at 275 nm was lower than that for other quinones which have values of 14,600 M$^{-1}$ cm$^{-1}$ in ethanol (Crane, 1971 above) and 12,250 M$^{-1}$ cm$^{-1}$ in aqueous buffer (Cabrini et al, *Arch Biochem Biophys*, 208, 11–19, 1981). While the absorbance of the quninone was about 10% lower in buffer than in ethanol, the discrepancy was not due to an interaction between the phosphonium and the quinone as the absorbance of the precursor quinone before linking to the phosphonium and that of the simple phosphonium methyltrihenylphosphonium were additive when 50 μM of each were mixed together in either ethanol or aqueous buffer. The $\Delta\epsilon_{ox-red}$ was 7,000 M$^{-1}$ cm$^{-1}$.

Figure 11:
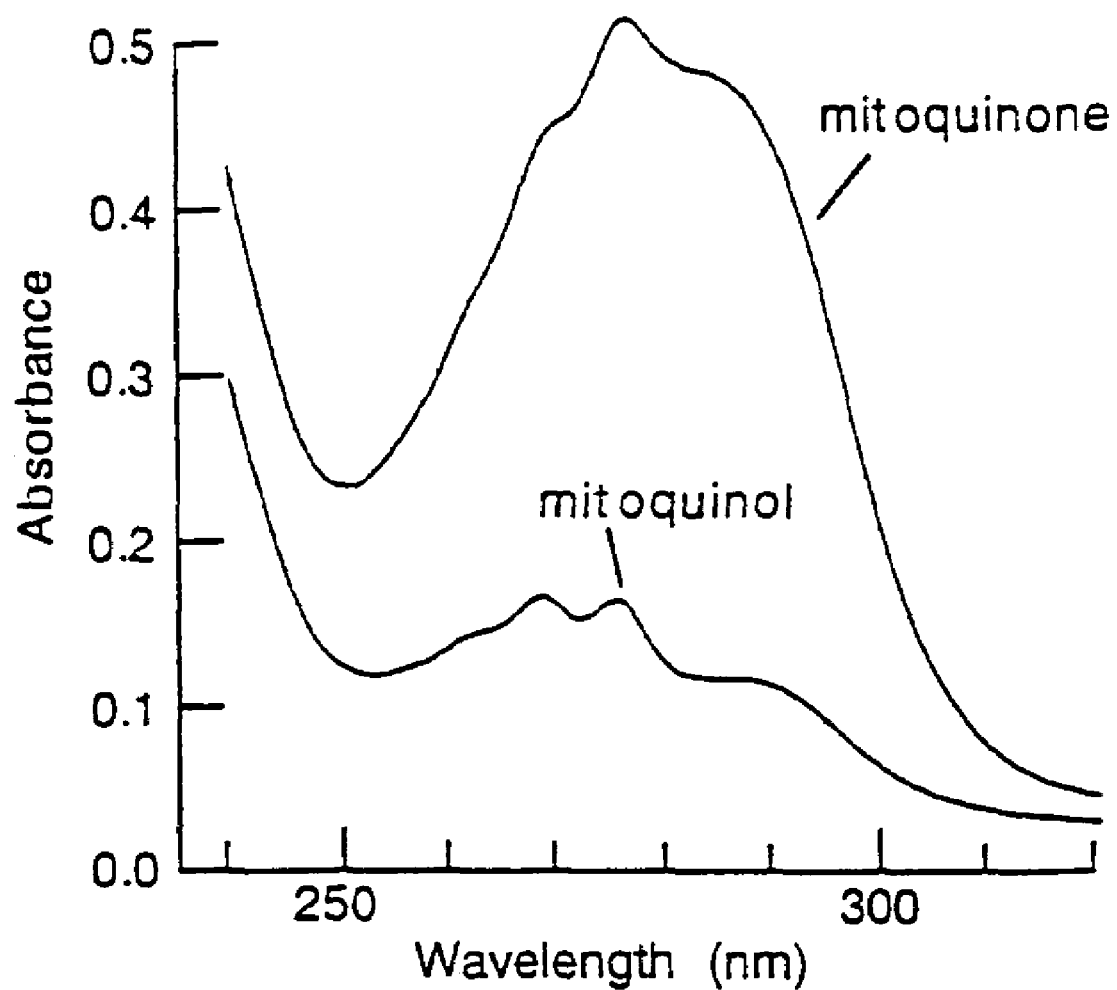
FIG. 11 shows the UV-absorption spectrum of [10-(6'-ubiquinonyl)decyltriphenyl-phosphonium bromide] (herein referred to as "mitoquinone") and of the reduced form of the compound [10-(6'-ubiquinolyl)decyltriphenylphosphonium bromide] (herein referred to as "mitoquinol").
Figure 12:
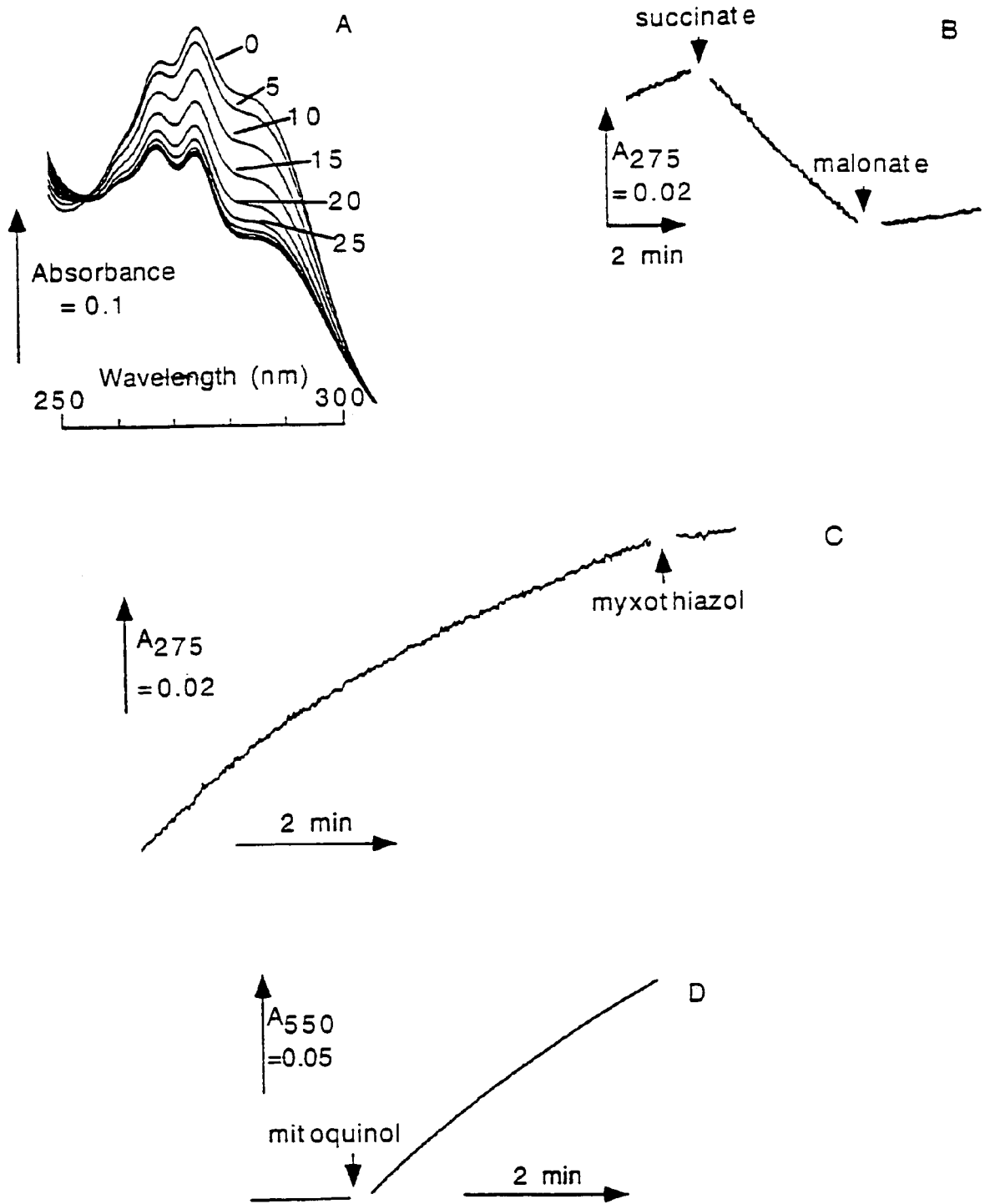
FIGS. 12A to 12D show reactions of [10-(6'-ubiquinonyl)decyltriphenylphosphonium bromide] ("mitoquinone") and the reduced form of the compound ("mitoquinol") with mitochondrial membranes. Beef heart mitochondrial membranes (20 µg/ml) were suspended in 50 mM sodium phosphate, pH 7.2 at 20° C. In panel A rotenone and antimycin were present and for the t=0 scan, then succinate (5 mM) was added and scans repeated at 5 minute intervals as indicated. In panel B $A_{275}$ was monitored in the presence of rotenone and antimycin and then mitoquinone (50 µM) was added, followed by succinate (5 mM) and malonate (20 mM) where indicated. In Panel C rotenone, ferricytochrome c (50 µM) and malonate (20 mM) were present, $A_{275}$ was monitored and mitoquinol (50 µM) and myxathiazol (10 µM) were added where indicated. In panel D $A_{550}$ was monitored and the experiment in Panel C was repeated in the presence of KCN. Addition of myxathiazol inhabited this rate by about 60–70%. There was no reaction between mitoquinone and succinate or NADH in the absence of mitochondrial membranes, however mixing 50 µM mitoquinone, but not mitoquinol, with 50 µM ferricytochrome c led to some reduction of $A_{550}$.

The spectrum of fully oxidised mitoquinone (50 μM) in 50 mM sodium phosphate, pH 7.2 is shown in FIG. 11. Addition of NaBH$_4$ gave the fully reduced compound, mitoquinol. The UV absorption spectrum of the reduced (quinol) and oxidised (quinone) mitoquinone/ol are shown in FIG. 11. To determine whether the mitochondrial respiratory chain could also oxidise or reduce the compound mitoquinone was incubated with beef heart mitochondrial membranes (FIG. 12). In panel A the spectrum of fully oxidised mitoquinone in the presence of antimycin inhibited membranes is shown (t=0; FIG. 12A). Addition of succinate led to the gradual reduction of the mitoquinol as measured by repeating the measurement every five minutes and showing that the peak at 275 nm gradually disappeared, the presence of antimycin prevented the oxidation of the quinol by mitochondrial complex III. Succinate did not lead to the complete reduction of mitoquinone to mitoquinol, as can be seen by comparing the complete reduction brought about by borohydride (FIG. 11), instead it reduced about 23% of the added ubiquinone (FIG. 12A). This is presumably due to equilibration of the quinol/quinone couple with the succinate/fumarate couple (Em Q=40 mV at pH 7, Em Suc=30 mV), hence this proportion corresponds to an Eh of about +8 mV.

The reduction of mitoquinone can be followed continuously at A$_{275}$ nm (FIG. 12B). On addition to rotenone inhibited mitochondrial membranes the small amount of mitoquinol remaining was oxidised leading to a slight increase in A275, but on addition of the Complex II substrate succinate mitoquinone was rapidly reduced and this reduction was blocked by malonate, an inhibitor of Complex II (FIG. 12B). The rate of reduction of mitoquinone was 51±9.9 nmol/min/mg protein, which compares with the rate of reduction of cytochrome c by succinate in the presence of KCN of 359 nmol/min/mg. Allowing for the 2 electrons required for mitoquinone reduction compared with 1 for cytochrome c the rate of electron flux into the mitoquinone pool is of similar order to the electron flux through the respiratory chain.

To determine whether mitoquinol was oxidised by Complex III of the respiratory chain, mitoquinol was added to beef heart membranes which had been inhibited with rotenone and malonate (FIG. 12C). The mitoquinol was oxidised rapidly by membranes at an initial rate of about 89±9 mmol mitoquinol/min/mg protein (mean of 2+/−range) and this oxidation was blocked by myxathiazol an inhibitor of complex III (FIG. 12C). To confirm that these electrons were being passed on to cytochrome c, mitoquinol was then added to membrane supplemented with ferricytochrome c and the rate of reduction of cytochrome c monitored (FIG. 12D). Addition of mitoquinol led to reduction of cytochrome c at an initial rate of about 93+/−13 nmol/min/mg (mean+/−range). This rate was largely blocked by myxathiazol, although a small amount of cytochrome c reduction (about 30–40%) was not blocked by myxathiazol.

Figure 13:
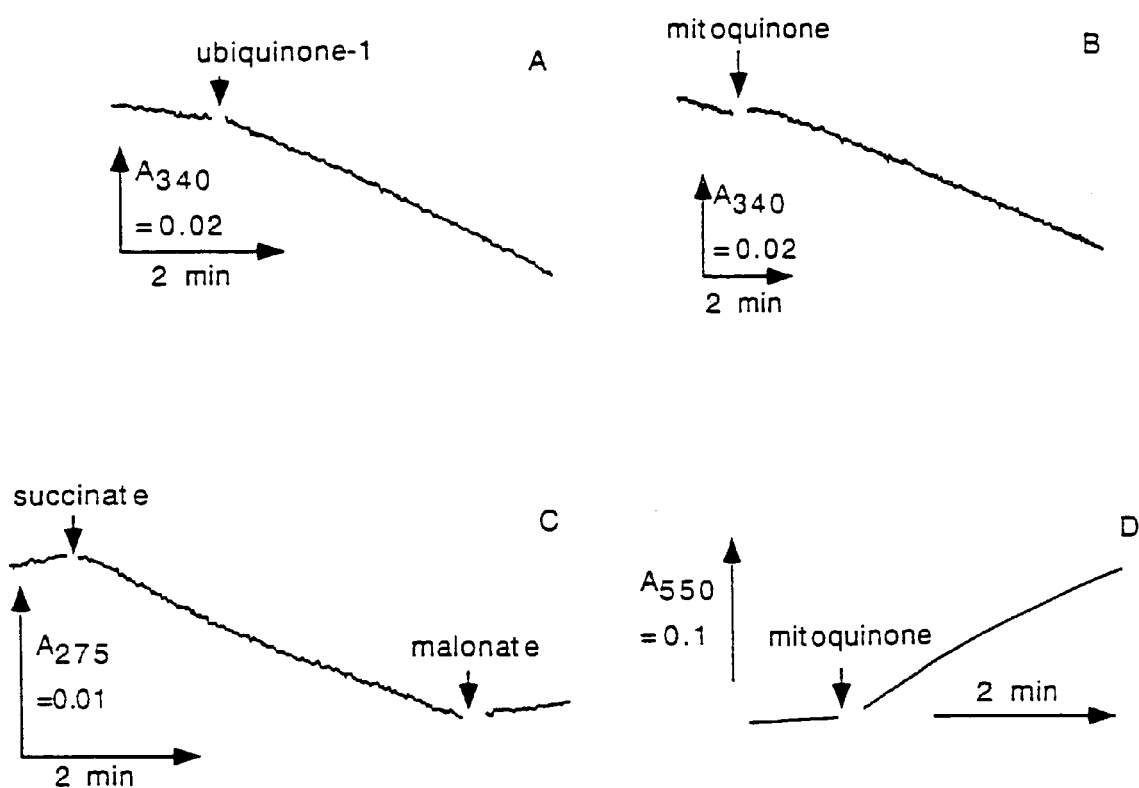
FIG. 13 shows reactions of mitoquinol and mitoquinone with pentane-extracted mitochondrial membranes. Pentane extracted beef heart mitochondria (100 µg protein/ml) were suspended in 50 mM sodium phosphate, pH 7.2 at 20° C. In Panel A NADH (125 µM) was added and $A_{340}$ was monitored and ubiquinone-1 (UQ-1; 50 µM added where indicated. This was repeated in Panel b, except that mitoubiquinone (50 µM) was added. In Panel C pentane extracted mitochondria were incubated with mitoquinone (50 µM), $A_{275}$ was monitored and succinate (5 mM) and malonate (20 mM) added where indicated. In Panel D pentane-extracted mitochondria were incubated with NADH (125 µM), ferricytochrome c (50 µM) and $A_{550}$ was monitored and mitoquinone (50 µM) was added where indicated. Addition of myxathiazol inhibited the rate of reduction by about 60–70%.

Mitoquinone/ol may be picking up and donating electrons directly from the active sites of the respiratory complexes, or it could be equilibrating with the endogenous mitochondrial ubiquinone pool. To address this question the endogenous ubiquinone pool was removed from beef heart mitochondria by pentane extraction. In the absence of endogenous ubiquinone as an electron acceptor the pentane extracted beef heart mitochondria could not oxidise added NADH, but addition of ubiquinone-1, a ubiquinone analogue that can pick up electrons from the active site of complex I, the oxidation of NADH is partially restored (FIG. 13A). Similarly, addition of mitoquinone also restored NADH oxidation indicating that mitoquinone can pick up electrons from the complex I active site (FIG. 13B). Succinate could also donate electrons to mitoquinone in pentane extracted beef heart mitochondrial in a malonate sensitive manner, suggesting that mitoquinone could also pick up electrons from the active site of Complex II (FIG. 13C). Finally, the effect of the quinone on the flux of electrons to cytochrome c was determined and it was shown that there was no NADH-ferricytochrome c activity until mitoquinone was added (FIG. 13D), and this was partially inhibited by myxathizol (60–70%).

Figure 14:
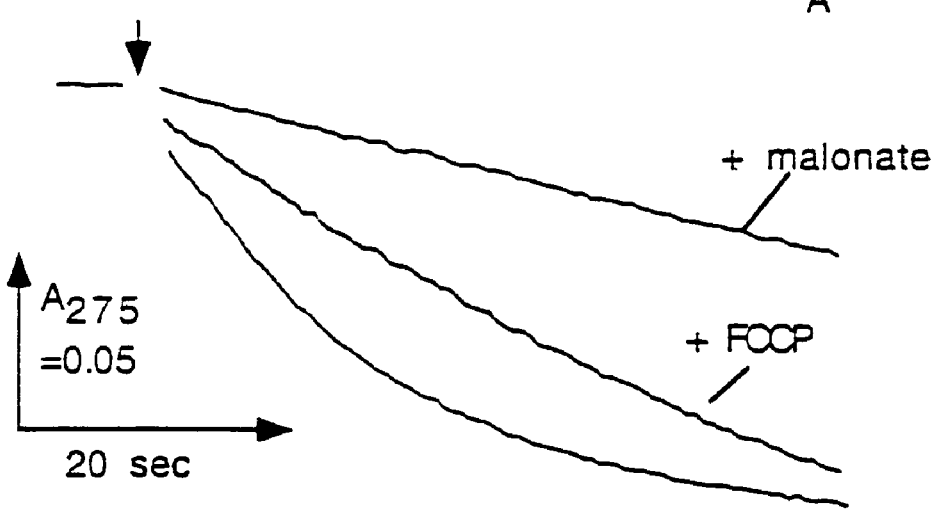
FIG. 14 shows reduction of mitoquinone by intact mitochondria. Rat liver mitochondria (100 µg/ml) were incubated in 120 mM KCl, 10 mM HEPES, 1 mM EGTA, pH 7.2 at 20° C. and $A_{275}$ monitored. In panel A rotenone and succinate (5 mM) were present and mitoquinone (50 µM) was added where indicated. This experiment was repeated in the presence of malonate (20 mM) or FCCP (333 mM). In panel B glutamate and malate (5 mM of each) were present from the start and and mitoquinone (50 µM) was added where indicated. This experiment was repeated in the presence of FCCP or with rotenone and FCCP. Addition of TPMP (50 µM) instead of mitoquinone did not lead to changes in $A_{275}$.
Figure 14:
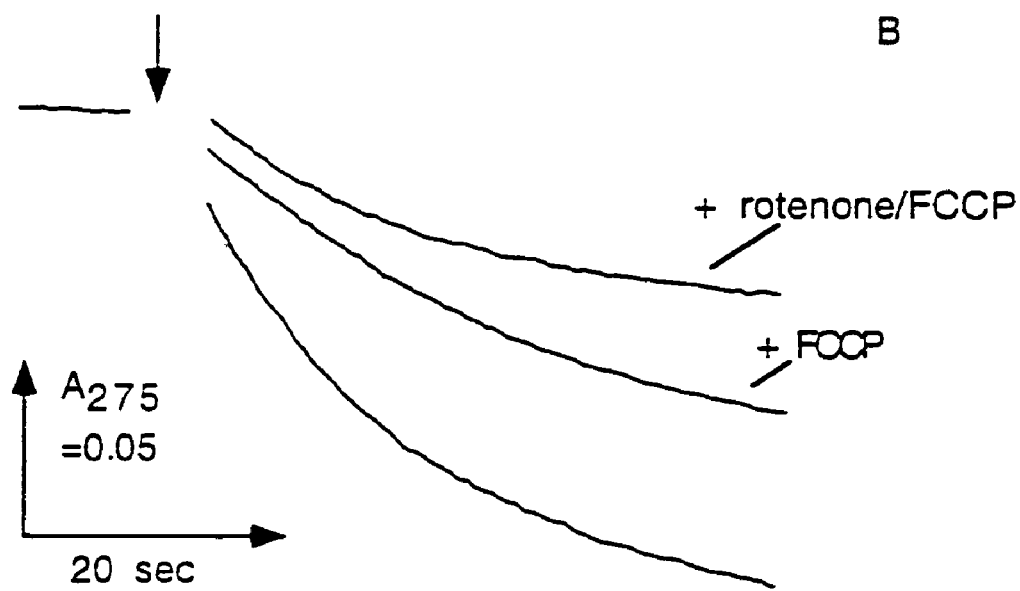

The next step was to see if mitoquinone also accepted electrons within intact mitochondria (FIG. 14). When mitoquinone was added to intact energised mitochondria it was rapidly reduced (FIG. 14A). In the presence of the uncoupler FCCP to dissipate the membrane potential the rate was decreased about 2–3 fold, presumably due to the prevention of the uptake of the compound in to the mitochondria (FIG. 14A). The complex II inhibitor malonate also decreased the rate of reduction of mitoquinone (FIG. 14A). Use of the NADH-linked substrates glutamate/malate also led to the rapid reduction of mitoquinone by intact mitochondria which again was decreased by addition of the uncoupler FCCP (FIG. 14B). The Complex I inhibitor rotenone also decreased the rate of reduction of mitoquinone (FIG. 14B).

Figure 15:
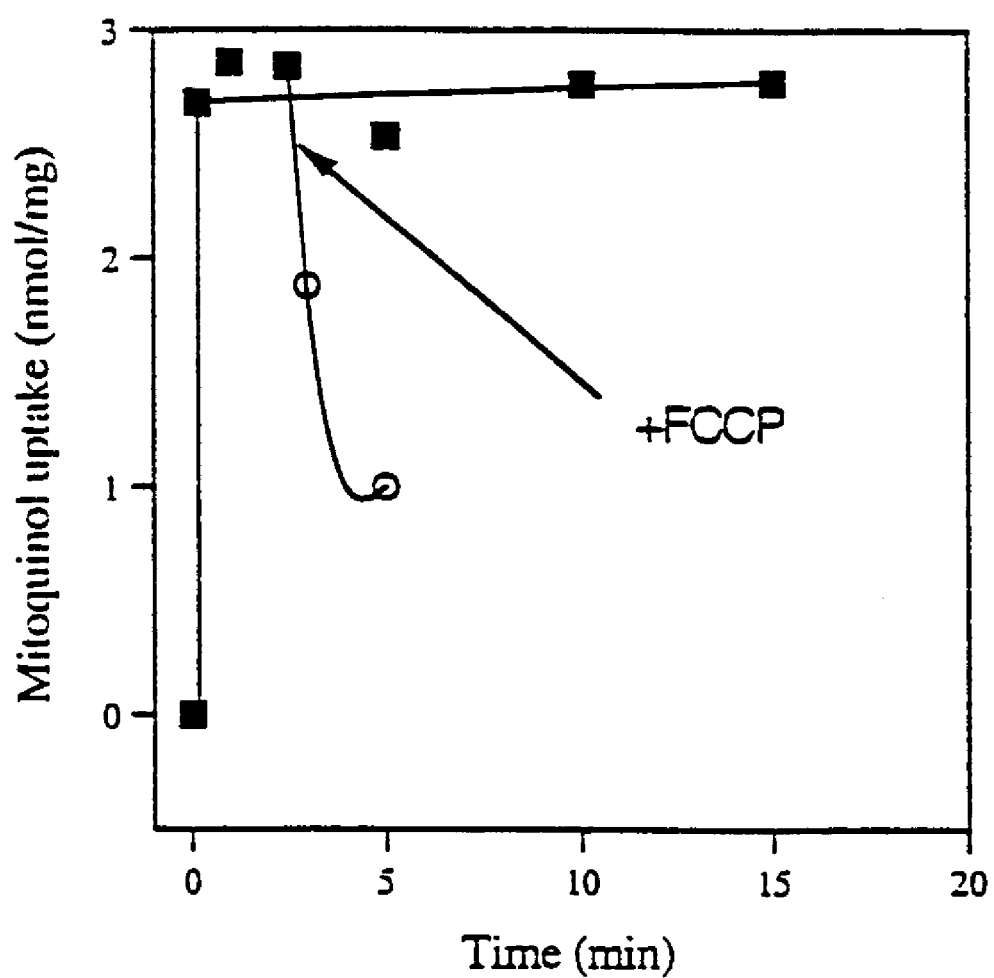
FIG. 15 shows uptake of radiolabelled mitoquinol by energised rat liver mitochondria and its release on addition of the uncoupler FCCP.

The next step was to see if mitoquinol was accumulated by energised mitochondria. To do this a tritiated version of the compound was made, incubated with energised mitochondria and the amount taken up into the mitochondria determined. It can be seen that the compound is accumulated rapidly and that this accumulation is reversed by addition of the uncoupler FCCP (FIG. 15).

Figure 16A:
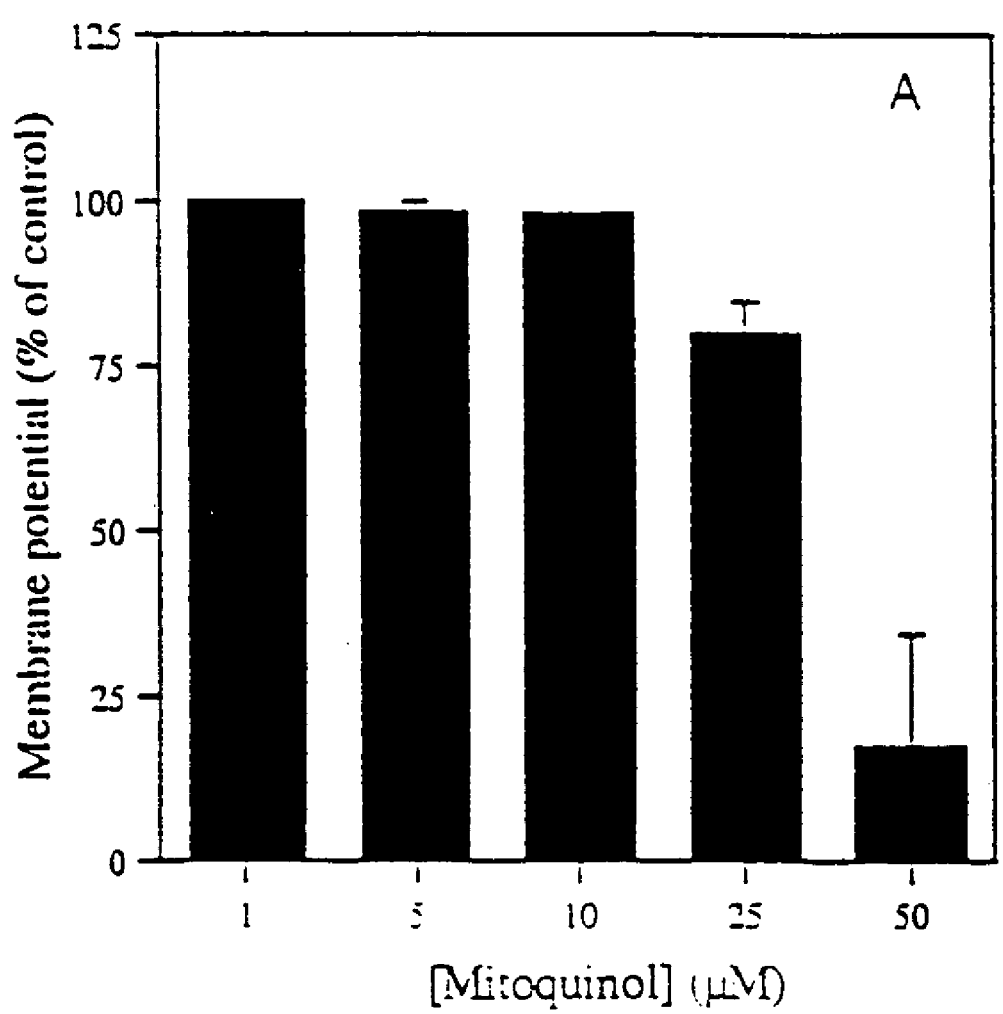
FIG. 16 shows the effect of mitoquinol on isolated rat liver mitochondria. In A rat liver mitochondria energised with succinate were incubated with various concentrations of mitoquinol and the membrane potential determined as a percentage of control incubations. In B the respiration rate of succinate energised mitochondria under state 4 (black), state 3 (white) and uncoupled (stippled) conditions, as a percentage of control incubations.
Figure 16B:
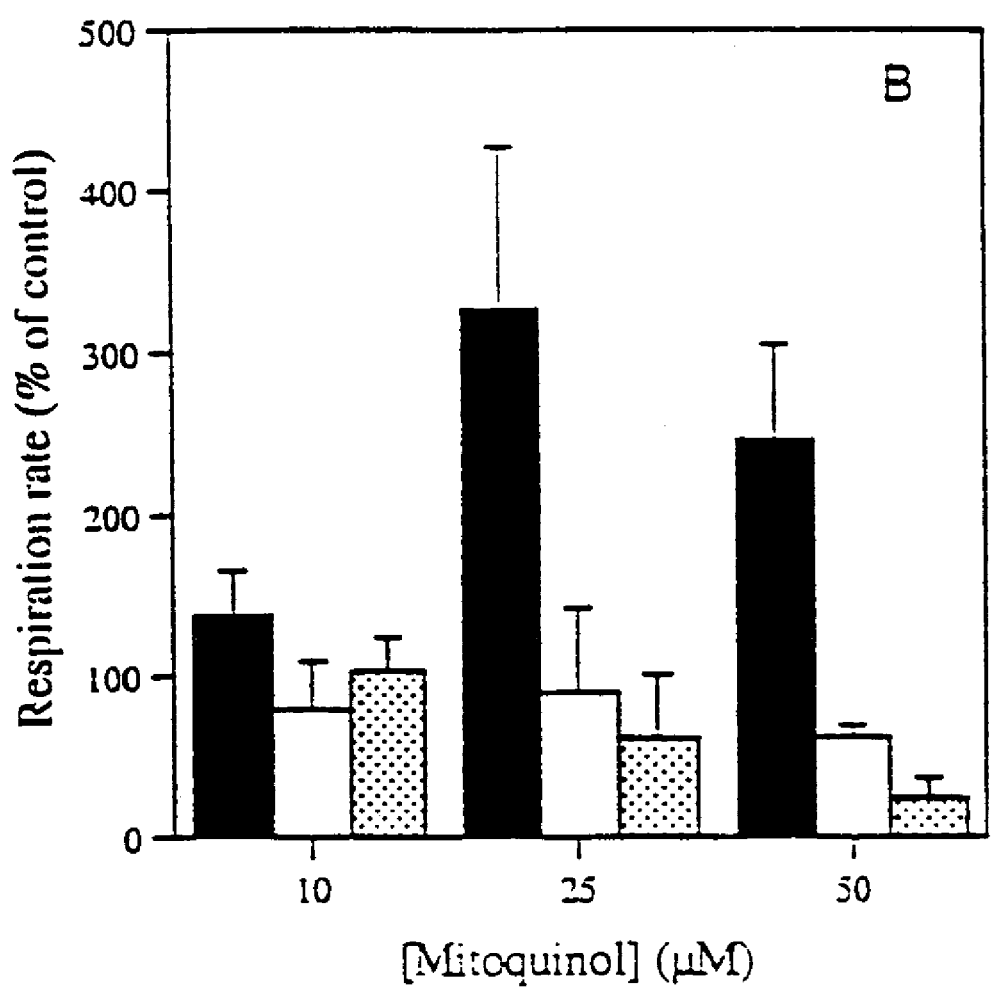

The next assays were to determine the toxicity of these compounds to mitochondria and cells. To determine the toxicity to isolated mitochondria the effect on membrane potential and respiration rate were measured (FIG. 16). It can be seen from FIG. 16 that 10 μM mitoquinol had little effect on mitochondrial function and at 25 μM and above there was some uncoupling and inhibition of respiration.

INDUSTRIAL APPLICATION

The compounds of the invention have application in selective antioxidant therapies for human patients to prevent mitochondrial damage. This car; be to prevent the elevated mitochondrial oxidative stress associated with particular diseases, such as Parkinson's disease, diabetes or diseases associated with mitochondrial DNA mutations. They could also be used in conjunction with cell transplant therapies for neurodegenerative diseases, to increase the survival rate of implanted cells.

In addition, these compounds could be used as prophylactics to protect organs during transplantation, or ameliorate the ischaemia-reperfusion injury that occurs during surgery. The compounds of the invention could also be used to reduce cell damage following stroke and heart attack or be given prophylactically to premature babies, which are susceptible to brain ischemia. The methods of the invention have a major advantage over current antioxidant therapies—they will enable antioxidants to accumulate selectively in mitochondria, the part of the cell under greatest oxidative stress. This will greatly increase the efficacy of antioxidant therapies. Related lipophilic cations are being trialed as potential anticancer drugs and are known to be relatively non-toxic to whole animals, therefore these mitochondrially-targeted antioxidants are unlikely to have harmful side effects.

Those persons skilled in the art will appreciate that the above description is provided by way of example only, and that different lipophilic cation/antioxidant combinations can be employed without departing from the scope of the invention.

What is claimed is:

1. A pharmaceutical composition suitable for the treatment of a patient who would benefit from reduced oxidative stress, which comprises a mitochondrially-targeted antioxidant compound in combination with one or more pharmaceutically acceptable carriers or diluents, wherein the mitochondrially-targeted antioxidant compound comprises a triphenylphosphonium cation covalently coupled to an antioxidant moiety, wherein the antioxidant moiety is capable of being transported through the mitochondrial membrane and accumulated within the mitochondria of intact cells, with the proviso that the mitochondrially-targeted antioxidant compound is not thiobutyltriphenylphosphonium bromide.

2. The pharmaceutical composition of claim 1 wherein the mitochondrially-targeted antioxidant compound has the formula

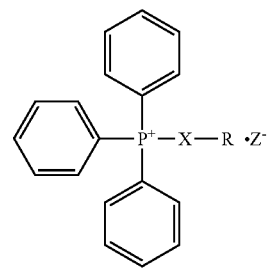

I wherein X is a linking group, Z is an anion, and R is an antioxidant moiety.

3. The pharmaceutical composition of claim 2, wherein X is a $C_1$ to $C_{15}$ carbon chain.

4. The pharmaceutical composition of claim 3 wherein X includes one or more double or triple bonds.

5. The pharmaceutical composition of claim 3 wherein X includes one or more substituents selected from the group consisting of a hydroxyl group, a carboxylic acid group and an amide group.

6. The pharmaceutical composition of claim 3 wherein X includes one or more unsubstituted or substituted alkyl, alkenyl or alkynyl side chains.

7. The pharmaceutical composition of claim 3 wherein the mitochondrially targeted antioxidant compound has the formula

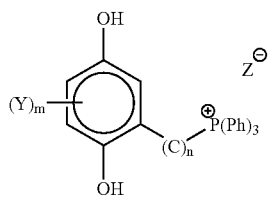

II wherein:
Z is a pharmaceutically acceptable anion,
m is 3,
each Y is independently selected from the group consisting of methoxy and methyl,
$(C)_n$ represents a carbon chain, and
n is an integer of from 1 to 15.

8. The pharmaceutical composition of claim 7 wherein the carbon chain includes one or more substituents selected from the group consisting of a hydroxyl group, a carboxylic acid group and an amide group.

9. The pharmaceutical composition of claim 7 wherein the carbon chain includes one or more unsubstituted or substituted alkyl, alkenyl or alkynyl side chains.

10. A pharmaceutical composition suitable for the treatment of a patient who would benefit from reduced oxidative stress, which comprises a mitochondrially-targeted antioxidant compound in combination with one or more pharmaceutically acceptable carriers or diluents, wherein the mitochondrially targeted antioxidant compound is:

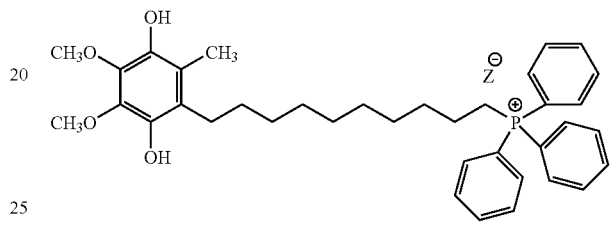

wherein Z is an anion.

* * * * *